(12) United States Patent
Kuvshinov et al.

(10) Patent No.: US 6,849,776 B1
(45) Date of Patent: Feb. 1, 2005

(54) MOLECULAR CONTROL OF TRANSGENE SEGREGATION AND ITS ESCAPE BY A RECOVERABLE BLOCK OF FUNCTION (RBF) SYSTEM

(75) Inventors: Viktor Kuvshinov, Helsinki (FI); Kimmo Koivu, Helsinki (FI); Anne Kanerva, Helsinki (FI); Eija Pehu, Helsinki (FI)

(73) Assignee: UniCrop Ltd, Helsinki (FI)

( * ) Notice: Subject to any disclaimer, the term of this patent is extended or adjusted under 35 U.S.C. 154(b) by 0 days.

(21) Appl. No.: 09/617,543

(22) Filed: Jul. 14, 2000

(51) Int. Cl.[7] .................. C12N 15/82; C12N 15/31; C12N 15/55; A01H 5/00; A01H 1/00
(52) U.S. Cl. .................. 800/278; 800/260; 800/271; 800/274; 800/287; 800/288; 435/199; 435/320.1; 435/419; 435/468; 536/23.2; 536/23.7
(58) Field of Search ................... 800/260, 271, 800/274, 278, 287, 288, 290; 435/199, 320.1, 419, 468, 69.1, 418; 536/23.2, 23.7, 23.6

(56) References Cited

U.S. PATENT DOCUMENTS

| | | | | |
|---|---|---|---|---|
| 5,689,041 A | * | 11/1997 | Mariani et al. | 800/205 |
| 5,880,333 A | * | 3/1999 | Goff et al. | 800/288 |

FOREIGN PATENT DOCUMENTS

| | | |
|---|---|---|
| WO | 94 03619 | 2/1994 |
| WO | WO 97/30162 | 8/1997 |
| WO | 00 37660 | 6/2000 |

OTHER PUBLICATIONS

Williams, M. Tibtech 13:344–349, Sep. 1995.*
Kriete et al. Plant Journal 9(6): 809–818, 1996.*
Viktor Kuvshinov, "Development of Transgenic Crops Protected from Insect Damage and Transgene Escape", *Academic Dissertation in Genetics*, University of Helsinki, Finland, Mar. 16, 2001.
Harue Akasofu et al., "Nucleotide Sequence of the Gene for the *Vigna mungo* Sulfhydryl–endopeptidase (SH–EP)", *Nucleic Acids Research*, 1990, vol. 18, No. 7, obtained from website http://srs6.ebi.ac.uk/srs6bin/cgi–bin/wgetz?-e+em-bl–id:VMSHEPGO on Oct. 25, 2001; p. 1892 of N.A.R.
Kuvshinov et al. 2001, Plant Science 160:517–522.
Kuvshinov et al. 1999. Plant Cell Reports 18:773–777.
Shevelev et al. 1997. FEBS Letters 404:148–152.
Kuvshinov et al. 2001. Plant Science 160:341–353.
Jonathan Gressel, "Tandem Constructs: Preventing The Rise Of Superweeds" Tibtech. vol. 17, pp. 361–366, Sep. 1999.
Abstract —Williams et al., "Maintenance of male–sterile plants", U.S. Appl. No. 5,750,867, Date Issued May 12, 1998, only.
Abstract —De Greef et al., "Plants with modified flowers seeds or embryos", U.S. Appl. No. 5,767,374, Date Issued Jun. 16, 1998, only.
Abstract —Fabijanski et al., "Molecular methods of hybrid seed production", U.S. Appl. No. 6,013,859, Date Issued Jan. 11, 2000, only.
Abstract —Van Tunen et al., "Male–sterile plants, methods for obtaining male–sterile plants and recombinant DNA for use therein", U.S. Appl. No. 6,005,167, Date Issued Dec. 21. 1999, only.
Abstract —Oliver et al., "Control of plant gene expression", U.S. Appl. No. 5,723,765, Date Issued Mar. 3, 1998, only.
Abstract —Goff et al, "Control of gene expression in plants by receptor mediated transactivation in the presence of a chemical ligand" U.S. Appl. No. 5,880,333, Date Issued Mar. 9, 1999, only.
Abstract —Poovaiah et al., "Control of growth and development of potato plants", U.S. Appl. No. 5,498,533, Date Issued Mar. 12, 1996, only.
Henry Daniel, "Molecular Strategies for Gene Containment In Transgenic Crops", *Nature Biotechnology*, Jun. 2002, pp. 581–586, vol. 20.

* cited by examiner

*Primary Examiner*—David T. Fox
(74) *Attorney, Agent, or Firm*—Dodds and Associates

(57) ABSTRACT

The invention is related to a method and a DNA construct for controlling transgene segregation in a sexually reproducing multicellular organism (SRMO), especially in such SRMOs which are susceptible of interbreeding with their cultured or wild-type relatives. The method and construct allows the farmer to reuse the transgenic crop without risk for escape of the transgene into the environment. The DNA construct is a recoverable block of function (RBF) system comprising at least one blocking construct (BC), and at least one means for recovering the blocked functions. The BC has a capacity of blocking at least one molecular or physiological function essential for the development and/or reproductive cycle of the SRMO. The BC is closely linked to the transgene of intereset (TGI). The blocked function is recoverable by an external treatment or intervention, which is optionally combined with one or more recovering constructs (RC). Different types of RBFs, including single, full, delayed, double, multiple and reversed delayed RBF are disclosed.

25 Claims, 14 Drawing Sheets

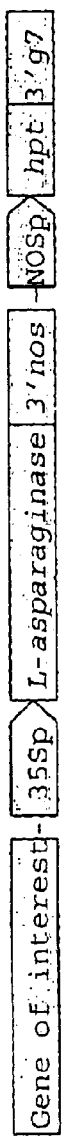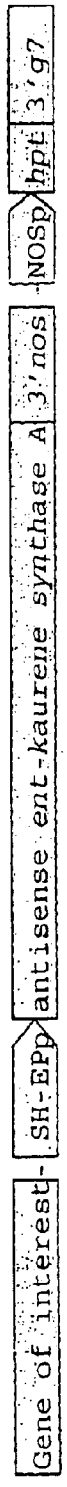
Fig. 1A
Fig. 1B
Fig. 1C
Fig. 1D

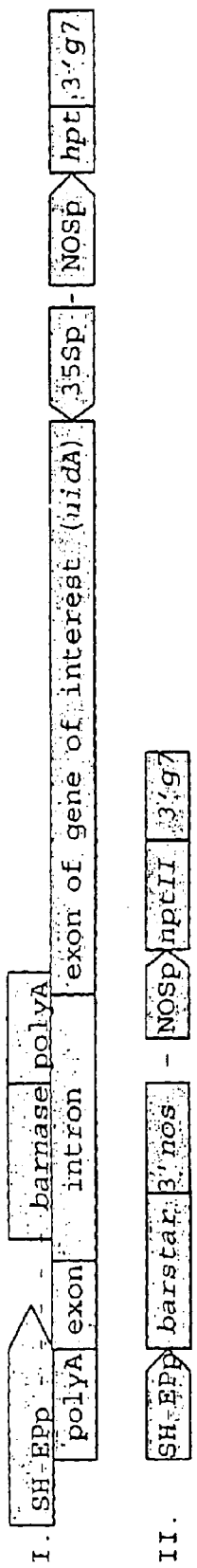
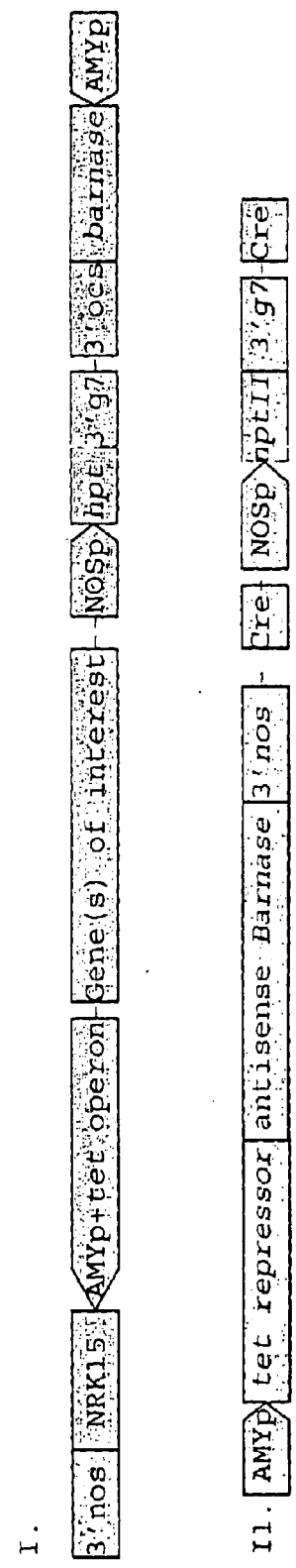
Fig. 2A
Fig. 2B

Fig. 3

```
       Barnase                                                                    uidA
gene
       gene nt      SphI    >SH-EP promoter from Vigna mungo>                        nt
       ...↓↓...CAGCATGCAAGAGAAAGATGATTCTTGAAGCATACGATAACAGATTGAATGTGACAAAAA          ↓↓
       -442    ----------+----------+----------+----------+----------+----------+
       ... ...  ..GTCGTACGTTCTCTTTCTACTAAGAACTTCGTATGCTATTGTCTAACTTACACTGTTTTT GTTTGTGTCTCAGCTTCAGGGTCGGCACCTAATACAAAAGGAAAATTTGTCAGGTTTCCT
       -382    ----------+----------+----------+----------+----------+----------+
               CAAACACAGAGTCGAAGTCCCAGCCGTGGATTATGTTTTCCTTTTAAACAGTCCAAAGGA
                                                    <FUE<

TCCGTAGTTTCATTCACTATTATTGAATCCTTTGGCTACCATTCTTGAGAAACACAAACA
       -322    ----------+----------+----------+----------+----------+----------+
               AGGCATCAAAGTAAGTGATAATAACTTAGGAAACCGATGGTAAGAACTCTTTGTGTTTGT

>CAAT box>
               CTTCTTATATCTGTTCTACACAATTCTCTGAGTGCGTGCCACAGTTTGGTATCTTCATGA
       -262    ----------+----------+----------+----------+----------+----------+
               GAAGAATATAGACAAGATGTGTTAAGAGACTCACGCACGGTGTCAAACCATAGAAGTACT >CAAT box>
               TTGCTCATTGTTCATGCCCATAAGGAACATGTAACTTCCTCATTTATTTATTATTGCTTT
       -202    ----------+----------+----------+----------+----------+----------+ 2291
               AACGAGTAACAAGTACGGGTATTCCTTGTACATTGAAGGAGTAAATAAATAATAACGAAA
                      ↑PolyA ↑ cleavage ↑                < NUE< NUE <

SpeI                 > TATA box  >
               TGTTTTCTTCTCACTAGTTTACAAACGTTTCCCTATATAAACCCTCCTTTGTTCACTGCT
       -142    ----------+----------+----------+----------+----------+----------+ 2231
               ACAAAAGAAGAGTGATCAAATGTTTGCAAAGGGATATATTTGGGAGGAAACAAGTGACGA
                                <FUE<                             <Stop< uidA
                                                                 >5'UTR
               TTCCTCCCTGCTGTGGCTTCTCTCCGAAGTTCATCCCGGTCCACCTGCAAAATAAGTAAT
       -82     ----------+----------+----------+----------+----------+----------+ 2171
               AAGGAGGGACGACACCGAAGAGAGGCTTCAAGTAGGGCCAGGTGGACGTTTTATTCATTA
                     exon              uidA                  ↑<3'intron<   intron
                          +1 Start barnase
               AAGATAAAGTAAAAAAGTTAGTATGGCTCAAGTTATTAATACTTTTGATGGAGTTGCTGA
       -22     ----------+----------+----------+----------+----------+----------+ 2111
               TTCTATTTCATTTTTTCAATCATACCGAGTTCAATAATTATGAAAACTACCTCAACGACT
                                    <branch point<           intron of uidA TTATCTTCAAACTTATCATAAACTTCCAGATAATTATATTACTAAATCTGAAGCTCAAGC
       +39     ----------+----------+----------+----------+----------+----------+ 2051
               AATAGAAGTTTGAATAGTATTTGAAGGTCTATTAATATAATGATTTAGACTTCGAGTTCG TCTTGGATGGGTTGCTTCTAAAGGAAATCTTGCTGATGTTGCTCCAGGAAAATCTATTGG
       +99     ----------+----------+----------+----------+----------+----------+ 1991
               AGAACCTACCCAACGAAGATTTCCTTTAGAACGACTACAACGAGGTCCTTTTAGATAACC AGGAGATATTTTTTCAAATAGAGAAGGAAAACTTCCAGGAAAATCTGGAAGAACATGGAG
       +159    ----------+----------+----------+----------+----------+----------+ 1931
               TCCTCTATAAAAAGTTTATCTCTTCCTTTTGAAGGTCCTTTTAGACCTTCTTGTACCTC
```

Fig. 3 (continued)

```
         AGAAGCTGATATTAATTATACTTCTGGATTTAGAAATTCAGATAGAATCCTTTATTCATC
+219     ------------+----------+----------+----------+----------+----------+ 1871
         TCTTCGACTATAATTAATATGAAGACCTAAATCTTTAAGTCTATCTTACGAAATAAGTAG barnase      >Stop>
         TGATTGGCTTATTTATAAAACTACAGATCATTATCAAACTTTTACAAAAATTAGATAAAT
+279     ------------+----------+----------+----------+----------+----------+ 1811
         ACTAACCGAATAAATATTTTGATGTCTAGTAATAGTTTGAAAATGTTTTTAATCTATTTA >FUE>    >FUE>       BclI    >NUE>                         PstI
         ATTTGTATTTTTGTATGTTGTGATCATTAATAAATAAATAAATACATACCTCTTCTGCA
+339     ------------+----------+----------+----------+----------+----------+ 1751
         TAAACATAAAAAACATACAACACTAGTAATTATTTATTTATGTATGGAGAAGACGT
                    intron                      <3'intron<  ↑  exon uidA ↓ PolyA   ↓cleavage
         GCAGGAAGGCAGCCGA... ... ...
+369     ------------+------ 1735
         CGTCCTTCCGTCGGCT... ... ...
            <uidA<
```

MOLECULAR CONTROL OF TRANSGENE SEGREGATION AND ITS ESCAPE BY A RECOVERABLE BLOCK OF FUNCTION (RBF) SYSTEM

TECHNICAL FIELD OF THE INVENTION

The present invention is related to a method and a DNA construct for controlling segregation of transgenes, allowing farmers to reuse their crop without risking the escape of transgenes into the environment The control is achieved by a recoverable block of function (RBF) system comprising a blocking construct and a means for recovering the blocked function. The present invention also relates to said RBF system as well as to its use in the production of transgenic sexually reproducing multicellular organisms (SRMO), especially plants and certain animals, such as fish.

BACKGROUND OF THE INVENTION

Over the past few years the concern of safety of transgenic crop production has attracted significant attention among the scientific community and the public at large. Several reports have shown pollen of transgenic plants may be spread from the field plots. Most problematic are crop species having wild relatives capable of hybridizing with the transgenic crop. Species such as *Brassicae* or various woody plants are good examples of high-risk groups. Even if the potential problem at present has been restricted to plants, it is likely that similar problems will be encountered when animals, such as fish, become more serious targets of transgenic production. It is also likely that a wide range of modifications will be applied to transgenic plants in the future thus intensifying the need to prevent transgene escape.

While the potential risks to human or animal health of a particular transgene and its product can be tested and measured, the impact of gene escape is more complex to assess. On the other hand, the potential value of transgenic improvement of crops is so large that rather than banning the use of transgenes is it is more productive to find solution to prevent gene escape.

Due to the great concern of transgene escape, several approaches to handle the problems have been presented. The first approach comprises plants with engineered sterility. The second involves control of seed germination, also referred to as "terminator technology" launched by Monsanto (U.S. Pat. No. 5,723,765). Additionally there are reports of application of conditionally lethal factors, also called suicidal genes.

Several groups have studied the use of engineered male (or female) sterility. In the male sterility (MS) method pollination is prohibited, for example, by arresting mRNA synthesis. Pollination can be restored by expression of a RNAase inhibitor. The recovering factor (RF) in said case is carried by the pollinating line, i.e. the two elements, MS and RF, are present in two different plant individuals. Only a hybrid of these two plant individuals carries both the blocking and the recovering factors and is therefore fertile. Thus, the male sterility technique is aimed to aid hybrid seed production. However, male sterility does not prevent escape of the transgene into the environment, because the pollinated female (MS) plants are capable to produce hybrid seeds, which may shatter and stay behind in the field after harvesting.

Engineered fertility control has also been achieved in transgenic *Brassica napus* by expression of the RNAase gene under an anther tapetum specific tobacco promoter (De Block and Debrouwer, (1993) Planta, 189: 218–225). Expression of the RNAase gene in the tapetum cells of the anther kills the pollen at early stages of development. Pollination of the male-sterile. flowers with pollen of transgenic *B. napus* plants expressing the RNAase gene under the same promoter recovers the male sterility (MS) trait and the hybrid plants can produce normal fertile pollen with expression of the two genes. U.S. Pat. No. 5,750,867 discloses the maintenance of male-sterile plants. U.S. Pat. No. 5,767,374 discloses a similar method for female-sterile (FM) plants in which method the ribonuclease gene is expressed in stamen cells of female parental plants and the killer gene expression in hybrid plants is restored by expression of the restorer gene coming from the pollinating parent line. The blocking gene is expressed in the female organs of the parent plant, while pollen remains fertile. The FM plants are intended to be pollinated by male sterile (MS) plants for production of hybrid seeds.

U.S. Pat. No. 5,728,926 discloses a method based on the expression of antisense mRNA of a gene vital for anther development. The antisense molecule is expressed at the same time with the sense molecule, both preferably driven by the same promoter. Concurrent expression of the sense and antisense orientations of the gene provides a silencing mechanism and thus prevents anther development. U.S. Pat. No. 6,013,859 discloses a method of hybridization. The blocking is provided by two consequent enzymatic reactions in the anthers or microspores. The pollinating parental line confers resistance to a selective marker (herbicide). U.S. Pat. No. 6,005,167 in turn describes a method for male or female sterility based on blocking, preferably by antisense technique, of the chalcone synthase expression in a developing anther or another part of the flower. Chalcone synthase is a key-enzyme in the flavonoid biosynthesis. Blocking the expression of this gene leads to unrecoverable blocking of fertilization.

U.S. Pat. No. 5,723,765 describes a method for arresting seed germination. The technique comprises activation of the inhibited blocking gene function through excision of a specific DNA sequence between the promoter and the blocking (terminator) gene by a specific Cre recombinase enzyme encoded by another gene placed under the Tet-repressed promoter. Seeds of transgenic plants not treated with tetracycline are capable of germinating under natural conditions. If the transgenic seeds are treated with tetracycline, the gene encoding for Cre recombinase is activated and it excises the DNA insertion between the LEA promoter and the toxin gene. Thus, the block is removed and the toxin activated. The toxin does not kill the plant immediately because the expression will be initiated only during late embryogenesis with the action of the LEA promoter.

The invention disclosed in U.S. Pat. No. 5,723,765 demonstrates inhibition of the development of seeds in the second generation. Without the mechanism of suppression, the 'killer' gene is activated during late stages of embryo development of the progeny and the seeds of the next generation do not germinate. The fundamental problem with said technique is that once the plants have been treated with tetracycline, i.e. the killer gene has been activated, they cannot be reused. Furthermore, if said transgenic plant carrying the tetracycline recoverable construct escapes into the environment, it is capable of germinating, growing to maturity, flowering and reproducing sexually. In other words, the transgene escape from transgenic plants is not prevented.

The technique described in U.S. Pat. No. 5,723,765 is often called "terminator" technique and it has encountered negative public attention because it gives the seed producing companies a possibility to control the market of transgenic seed production. Moreover, the technique does not prevent transgene escape.

Another related patent, U.S. Pat. No. 5,880,333 describes a method for regulating transgene expression through "receptor DNA cassettes" and chemical ligands activating the constructs. For example unrecoverable block (arrest) of embryo development has been achieved in *Brassica napus* by expression of the modified exotoxin A of *Pseudomonas aeruginosa* under napin promoter (Koning et al. 1992, Plant Mol. Biol., 18: 247–258). Pollen sterility has been achieved using diphtheria toxin A chain expression under lat52 promoter. Toxin expression leads to cell ablation in developing pollen (Twell, 1995, Protoplasma, 187: 144–154).

U.S. Pat. No. 5,498,533 describes the regulation of potato development by expression of sense and antisense constructs of the calmodulin gene. Expression of sense-oriented calmodulin gene increases shoot and tuber growth, whereas plants carrying antisense constructs exhibit decreased shoot and tuber growth. Therefore the expression of antisense calmodulin gene may be used as a factor blocking a physiological function.

In other words, various inventors have described different types of unrecoverable block of function systems intended to provide control of escape of transgenic plants. The main problem related to the above described methods and systems, is that they are unrecoverable. The seeds cannot be reused once the recovery system has been applied. A further limitation of some of the methods is that they require vegetative propagation, because fertilization or embryo development is arrested.

The object of the present invention is to provide a method and DNA-constructs for blocking a function. The blocked function is not recovered under natural conditions, but is capable of being recovered only when an external controllable treatment or intervention is applied. Thus, the present invention not only stops segregation and escape of trangene (s) into environment but also allows the farmer provided with the correct instructions to reuse his crop.

According to this disclosure the solution to the problem of transgene escape is achieved by providing a DNA construct preventing sexual reproduction in absence of an external treatment or intervention. Normal growth and sexual reproduction can be achieved by an external treatment or intervention per se or by applying a specific recovering DNA construct in the RBF system.

SUMMARY OF THE INVENTION

The present invention is related to a method for preventing the escape of a transgene into the environment by a molecular control mechanism comprising the steps of constructing a recoverable block of function system (RBF). The system comprises at least one blocking construct (BC), and at least one means for recovering the blocked functions. The BC has a capacity of blocking at least one function essential for the survival, development and/or sexual reproduction of a sexually reproducing multicellular organism (SRMO). The nucleotide sequence providing the blocking effect in the BC is closely linked to at least one transgene of interest TGI encoding a desired gene product. The step of recovering the blocked functions comprises at least one external, artificial controllable treatment or intervention in combination with at least one optional recovering construct (RC).

The transgenic SRMO is prevented from sexual reproduction or from producing viable progeny by the BC,which under natural, non-manipulated conditions arrests an essential function in said SRMO. The blocked function may be recovered in order to allow normal development, proliferation, growth and sexual reproduction of the transgenic SRMO for agricultural, horticultural, forestral, industrial or any other feasible purposes. The recovery takes place by applying, at least one externally applicable, artificial, controllable manipulation, treatment or intervention step, which at a susceptible moment in the development cycle of the SRMO recovers the blocked function.

The transgene is prevented from leaking into the environment through hybridization, interbreeding or crossing of the parental transgenic SRMO with its wild-type relatives or cultivated non-transgenic relatives, by expression of the BC. Under natural conditions expression of the BC arrests at least one essential function of the transgenic SRMO or any hybrids carrying said BC as long as no external treatment or intervention is provided. This control of segregation leads to the extinction of the transgene in the nature.

The present invention is also related to a DNA construct for preventing the segregation and escape of a transgene of a SRMO into the environment. Said DNA construct is a recoverable block of function (RBF) system; comprising at least one BC having at least one nucleotide sequence capable of blocking a certain molecular or physiological function of a transgenic SRMO.

Said blocking nucleotide sequence is closely linked to one or more TGIs. The RBF system may also comprise one or more optional RCs, which are regulatable by an external, artificial treatment or intervention In other words, the RBF system may function with or without the RC as long as some external means, i.e. treatment or manipulation step for recovering, is available.

Also contemplated are cloning vectors, DNA cassettes, cells and cell-lines as well as transgenic plants or non-human animals harboring one or more of the RBF constructs of the present invention. A novel polycloning site shown in SEQ ID NO:4 is also disclosed. The characteristic features of the present invention are defined in more detail in the claims.

SHORT DESCRIPTION OF THE DRAWINGS

FIGS. 1A–1D depicts the molecular constructs described in the Examples 1, 2 and 4. The constructs are drawn schematically to show the disposition principle of the genes.

FIGS. 2A–2B depicts the molecular constructs described in the Examples 4–5. The constructs are drawn to show the principle disposition of the genes.

FIG. 3 depicts the sequence of the barnase gene placed inside the intron of the uidA gene. The barnase gene construct is shown downstream and contains the SH-EP promoter (about last three hundred nucleotides are shown) coding sequence and polyadenylation signal sites.

TERMS USER IN THE INVENTION

Figure 4:
FIG. 4 depicts the molecular construct described in the Example.3. The construct is drawn schematically to show the principle disposition of the genes.

In the present disclosure most of the terms used have the same meaning as they generally have in the field of recombinant DNA techniques, molecular biology and in plant production related sciences. Some terms are however, used in a somewhat different way and are explained in more detail below.

The term "recoverable block of function (RBF)" means a conceptual molecular system or molecular control mechanism consisting of a blocking construct (BC) and a means for recovering or a recovering tool. RBF performs the control of segregation and prevents the escape of the transgene(s) of interest (TGIs) in the sexually reproducing multicellular organism (SRMO), i.e. plants or non-human animals to which the system is applicable. RBF is introduced into the SRMOs together with the TGIs by a process of genetic transformation.

The term "delayed RBF system" means a recoverable block of function, wherein the RC is situated in a different non-allelic chromosome apart from the BC and the TGIs. Accordingly, the blocking function begins to work in the second heterozygous hybrid generation, when the BC and RC segregate into different generative cells.

The term "double RBF" means that the TGI(s) is (are) situated between two BCs which may either be similar or different to each other.

The term "reversed delayed RBF (RD-RBF)" means that an additional BC is linked to a first RC and this additional BC is recovered with a second RC linked to the TGI and the first BC. RD-RBF controls the release of both the BCs and the RCs into environment.

The term "multiple RBF" means a system comprising three or more RBF systems placed in different non-allelic chromosomes. A preferred embodiment of said multiple RBF system is the "triple RBF" described in Example 7, but more complex systems may be constructed based on this disclosure.

The term "blocking construct (BC)" means a DNA or nucleotide sequence introduced into the SRMO and closely linked to the TGI. The BC has a capacity to block a particular molecular or physiological function of the host organism. Expression of the blocking nucleotide (DNA or RNA) sequence may lead to extinction or alteration of the phenotype or physiology of the host organism. Accordingly, the transgenic SRMO, becomes incapable of sexual reproduction under unmanipulated, natural conditions. Said nucleotide sequence together with the means for recovering, i.e. the recovering tool controls the transfer of TGIs to the following generations and accordingly, the spread of the gene(s) to the surrounding natural populations. The BC is favorably linked to the TGI and in an extreme case it is placed in the intron of the TGI. At least it must be situated in the same chromosome. The BC expresses in the host organism constitutively or in an organ-specific, development-specific or a spatiotemporal manner.

If two BCs either similar or different to each other and recoverable by the same or different recovering mechanisms are used, they are preferably situated at both sides of the TGI, thereby resulting in a double recoverable blocking of function (double RBF).

The action of the BC may be based on several different molecular mechanisms such as expression of:
- an enzyme with unusual organ- or development-specificity;
- antisense mRNA of an enzyme important in development or functioning of the SRMO;
- a toxin and/or;
- an enzyme producing a toxic metabolite such as an antibiotic.

The term "means for recovering" or "recovering tool" means a method for recovering the transgenic SRMO from the detrimental consequences of the action of the BC. The recovering tool may comprise one or more treatment or intervention steps leading to direct external compensation of the deficiency of a particular function or an outside stimulus activating one or more "recovering constructs (RC)" transformed into the genome of the SRMO. Thus, the recovering tool comprises at least one external treatment or intervention step combined with one or more optional RCs.

The term "recovering construct (RC)" means a DNA construct or nucleotide (DNA or RNA) sequence, which recovers, unblocks or releases the function blocked by the BC. The RC is introduced into the genome of the SRMO, separately or together with the BC and TGI or TGIs. The action of the RC is externally regulated. The RC does not act, in other words it lacks function during the life of the SRMO under non-treated, unmanipulated, natural conditions. "External control" of the function of the "recovering tool" may be provided by an outside stimulus of a responsive promoter. In the case of a "delayed RBF system", external regulation implies intraline crossing of the transgenic SRMOs to support the homozygous condition of the RBF.

If the RC is placed in the same chromosome as the BC it results in a full or general RBF system. According to the present invention, the RC should preferably be in the same individual as the BC, preferably placed in different, non-allelic chromosome, thereby resulting in a delayed RBF system.

The term "SRMO" means sexually reproducible multicellular organisms including both plants and animals. Preferred plants are flowering plants including both angiosperms and gymnosperms. Especially preferred are crop plants, such as cereals. Especially, SRMOs are sexually reproducing multicellular organisms, which can interbreed or cross with other cultivated or wild-type relatives. Preferred animals are for example fish, shrimps, snails, poultry, etc.

The term "transgene(s), nucleotide sequences or gene(s) of interest (TGIs)" means the DNA or nucleotide sequence (s), including RNA sequences, which encode a desired gene product, i.e. a protein or a enzyme or other substances, including metabolites, hormones, toxins, antibiotics, etc. obtainable as end-products by the action of the direct gene products. Said TGIs are introduced into the genome of the SRMO through genetic transformation.

The DNA sequences of interest or TGIs usually encode products or molecules useful in agriculture, horticulture, forestry and industry. Alternatively, the gene products have some other feasible applications. Generally, the DNA sequence of interest or TGI is foreign or heterologous to the SRMO, but sometimes homologous nucleic acid sequences may be used and inserted e.g. as multiple copies in order to obtain optional amounts of the desired substance. In other words, the DNA sequence of interest may consist of one gene or nucleotide sequence or multiples thereof. Alternatively, several different genes may be introduced as multicopies or tandem inserts.

"Blocking" is achieved by a BC, which may be regulatable by a molecular control mechanism, e.g. a nucleotide sequence the expression of which blocks a function essential for the survival, growth, development and/or sexual reproduction of the SRMO and is capable of arresting the development of the molecular machinery of the host organism at the level of DNA, mRNA, protein or metabolite. If the molecular machinery is applied at a susceptible or vulnerable moment in the developmental cycle of the SMRO, it results in death, phenotype alteration, untimely seed germination or flowering, incapability to form inflorescence, flowers or fruits, formation of dwarf phenotype or some other morphological change preventing free hybridization or interbreeding of the transgenic SRMO under natural conditions.

The external activatable molecular mechanisms are for example:

specific binding;

proteolysis;

protein-protein interaction;

expression of an enzyme capable of detoxifying a toxic metabolite or substance;

expression of a substance or metabolite capable of compensating a substance; and/or expression of a substance capable of interacting with a toxic metabolite;

The tern "natural conditions" means the growing conditions, having ambient temperature, humidity, irradiation, chemical background of soils during production of the SRMO growth in agriculture, horticulture, forestry or in the nature.

The term "preventing escape of a transgene into the environment" means that transgene leakage into the nature through hybridization, crossing or interbreeding of the parental transgenic organism with its wild-type or cultured non transgenic relatives is prevented In other words, the release of the transgene is prohibited. The transgenic organism is prevented from growing, reproducing sexually or developing viable progeny. This is achieved by allowing the BC to function under normal, natural, unmanipulated, treatment- or intervention-free conditions. Said natural, unmanipulated conditions arrest, destroy or destruct a function which is essential for the reproduction of the SRMO. By segregation, said essential function of the SRMO leads to the extinction of the transgene in nature.

"Removing the blocked function" means unblocking the blocked function or recovering the blocked function in order to allow normal growth and sexual reproduction of the SRMO for agricultural, horticultural, forestral, industrial or any other production purposes. The removal of the blocked function is obtainable by preferably artificial, controlled or regulated externally applicable means Said externally applicable means comprise manipulation steps, i.e. treatment or intervention, which are applied per se or which act via a RC.

The terms "external treatment" and "external manipulation" mean artificial interventions or actions which are different from those occurring naturally in the sites of crop growth or in the nature. The external treatment may for example be external application of a substance or metabolite. Such an external treatment will lead for example to:

repression of the promoter of the BC;

silencing of the blocking gene mRNA expression by antisense RNA technique;

allowance of the expression of a protein capable of inactivating the protein encoded by the BC;

external compensation of the deficiency caused by the blocking;

external or internal induction of a responsive recovering gene/protein;

constitutive expression of the nucleotide sequence of the RC;

compensation of a deficiency caused by expression of the BC;

expression of repressor peptide/protein binding the operon sequence, which controls the expression of the nucleotide sequence of the BC;

expression of antisense RNA of the nucleotide sequence of the BC further leading to activating a silencing mechanism of the BC;

expression of a protein inactivating the protein encoded by the BC;

expression of an enzyme producing a substance or metabolite capable of compensating the deficiency resulted by the action of the BC; and/or conversion of a toxic metabolite encoded by the BC into a non-hazardous product.

DETAILED DESCRIPTION OF THE INVENTION

The present invention is related to methods of molecular biology for controlling transgene segregation and release into the environment through a DNA construct, herein called a recoverable block of function (RBF) system in contrast to the known unrecoverable blocking systems. The RBF comprises a nucleotide sequence capable of blocking physiological or developmental functions of the SRMOs. The blocked function leads to either death of the SRMO or to a significant change in the physiology of the SRMO, further resulting in inability to reproduce. The blocked function of the SRMO may be molecular, biochemical or physiological in nature. Recovering of the blocked function comprises an external, artificial manipulation, i.e. a treatment or intervention, which is performed with or without a DNA construct enabling the transgenic plant or animal to overcome the block of the function. One application according to the present disclosure is to prevent the transgene escape through hybridization under natural conditions. The invention operates in the field of molecular biology, transgenic technology, plant biochemistry and physiology, and also in specific field of DNA synthesis and antisense technology.

The present invention describes a molecular control system for transgene expression or escape into the environment through the RBF system. The invention implies an original idea to link the TGI into a DNA construct(s) capable of blocking a particular function in a SRMO. The block leads to death of the SRMO or arrests the development or alters the phenotype or physiology of the SRMO under natural conditions. The block of function is recoverable by the action of a recovering tool, which may comprise an external treatment and optionally include a DNA construct encoding for an mRNA, a protein or an enzymatic product inducible by an external chemical or physical stimulus. Therefore, every SRMO including the parental line or any subsequent hybrid thereof carrying the TGI linked to the RBF will die or remain sterile under natural conditions, in absence of activation of the recovering tool. Plants or animals carrying the RBF can be recovered, i.e. the blocking removed, by a particular procedure at a certain stage of the development. The BC causing the blocking may comprise any nucleotide sequence encoding for a receptor, antisense RNA, nuclease, toxin, enzyme or other product. The BC should be linked to the TGI, as close as in the intron of the TGI, and/or at least, in the same chromosome. The factor or means removing the block of function may be an external means, including application of chemical substances such as amino acids, hormones, salicylic acid or physical means or factors including temperature, light, osmosis, gravitation, humidity. The recovering means may be externally regulatable transgenic sequences, such as receptors, antisense RNAs, boundaries, repressors or proteolytic proteins, including both enzymes and their products. The external control may be a stimulus activating a responsive promoter. In delayed RBF system the external control may be an intraline cross to support homozygous condition of the transgene(s). Expression of the BC may be constitutive or spatiotemporal, i.e. organ or development specific. Expression of the RC may be constitutive in a delayed RBF system or inducible by a certain stimulus depending on the mechanism of a particular RBF system.

The present invention discloses a method and a DNA construct for controlling transgene segregation in a SRMO and for preventing the escape of said transgene into the environment by a molecular mechanism. The RBF comprises at least one BC and at least one means for recovering the blocked functions. One or more TGIs encoding desired heterologous or homologous gene products are closely linked to the RBF-system.

The BC has a capacity to block at least one essential molecular or physiological function effecting the survival and/or reproductive cycle of a SRMO. Said BC comprises a nucleotide sequence which is closely linked to at least one TGIs.

The means for recovering the blocked function comprises at least one externally applicable, artificial and controllable treatment or intervention with or without one or more RCs.

The reproduction of the transgenic SRMO is prevented by allowing expression of the BC, whereby an essential function effecting the survival, development and/or reproduction of said transgenic SRMO is arrested and/or prevented.

The blocked function is recovered at a susceptible moment of the growth or developmental cycle of the SRMO in order to allow normal growth and reproduction of said SRMO for production purposes, including agricultural, horticultural, forest and/or industrial applications, by applying at least one externally applicable, artificial and controllable manipulation, treatment or intervention step.

If a transgenic SRMO is prone to interbreeding (crossing) with its cultured of wild-type relatives, the transgene segregation is controlled and/or the leakage of said transgene into nature is prevented by allowing expression of the BC, which arrests or alters at least one essential molecular or physiological function of the transgenic SRMO and prevents sexual reproduction.

In the method according to the present invention, the function affecting the survival, developmental and/or reproductive cycle is characterized by arresting the development, altering the phenotype or morphology of the transgenic SRMO in an organ-specific, spatiotemporal or constitutive manner, in such a way that sexual reproduction is prevented.

A suitable moment for removing the blocking effect by applying an external, artificial and controllable step of manipulation, treatment or intervention is a susceptible moment or stage in the developmental cycle of the SRMO, at which an organ-specific, spatiotemporal or constitutive morphological change prevents the SRMO from free hybridization and/or sexual reproduction under natural conditions. Examples of susceptible moments are seed germination, initiation of flowering, formation of inflorescence, flowers and/or fruits. The blocking occurs at the level of DNA, mRNA, protein or metabolite and results in death, phenotypic or physiological alteration.

According to the present invention the means for recovering the blocked function comprises:

(a) adding at least one external chemical substance, such as a metabolite or hormone or some other small molecule;

(b) applying at least one external chemical or physical stimulus capable of activating the optional RC;

(c) repressing the promoter of the BC;

(d) silencing the blocking gene mRNA expression by antisense RNA technique;

(e) allowing the expression of a protein capable of inactivating the protein encoded by the BC by an externally or internally activatable molecular mechanisms;

(f) allowing the expression of an enzyme capable of producing a metabolite inactivating the protein expressed by the BC;

(g) allowing the expression of an enzyme capable of inactivating a toxic substance or metabolite or an antibiotic produced by the enzyme; and/or (h) allowing the expression of an enzyme capable of producing a substance, hormone or a metabolite compensating the deficiency or alternation caused by the expression of the BC.

The externally or internally activatable molecular mechanism according to the present invention is selected from the group consisting of:

(i) specific nucleic acid/protein binding;

(ii) proteolysis;

(iii) protein-protein interaction;

(iv) expression of an enzyme capable of converting a substance into a non-hazardous one;

(v) expression of a substance or a metabolite capable of compensating or inactivating the toxic overproduced molecule or interacting with it; and/or (vi) providing an enzyme producing a toxic or overproduced chemical substance or metabolite.

According to the present invention the BC expresses in the host organism constitutively or in an organ-specific, developmental stage-specific or a spatiotemporal manner. The recovering occurs by steps of manipulation, treatment or intervention comprising:

(a) compensating externally the deficiency caused by the BC;

(b) inducing externally or internally a responsive recovering DNA, RNA, protein or metabolite;

(c) expressing constitutively the nucleotide sequence of the RC; and/or (d) expressing temporally the nucleotide sequence of the RC in case of delayed RBF.

In a double RBF system, the BC may be placed in the intron of the TGI or preferably the TGI may be placed in between of two BCs. The two BCs, are either similar to each other or they are different. They are recoverable by either the same or different recovering mechanisms. In a delayed RBF system the RC is placed in the same individual SRMO, but preferably in different non-allelic chromosomes.

The nucleic acid sequence present in the BC expresses an enzyme, which is characterized by an ability to destroy or overproduce a chemical substance, such as a metabolite with unusual organ- or development-specificity, said enzyme being for example L-asparaginase or L-glutaminase. The BC may also comprise a nucleic acid sequence, encoding an antisense mRNA of an enzyme, e.g. Ent-kaurene synthase A, which is important in development or fruit formation of the host plant. Alternatively, the BC may comprise a nucleic acid sequence encoding a nuclease or nucleic acid recombinase. Synthetic nucleotide sequence adapted to host preference and to an intron in a host nucleotide sequence encoding the desired product may be prepared. An example of such synthetic ribonuclease is barnase, the synthetic nucleotide sequence of which comprises SEQ ID NO:1, adapted to (host) plant preference and SEQ ID NO:3, adapted to plant intron preference.

The nucleotide sequence of the BC may also encode a protease or a toxin, such as Diphtheria toxin A or NPK15 protein kinase or an enzyme producing a toxic substance or metabolite, e.g. an antibiotic.

The means for recovering the block comprises applying externally a substance, metabolite or hormone to compensate deficiency affected by blocking construct. Such substances are for example gibberellins given externally to plants or antisense mRNA of ent-kaurene synthase A. A further means for recovering is expression of repressor peptide or protein binding the operon sequence controlling the expression of the blocking nucleotide sequence, such repressors and operons being for example the T10 tet repressor protein and the tet-operator DNA sequence. Still another means for recovering is the expression of antisense RNA of the blocking nucleotide sequence activating a silencing mechanism of the BC expression, wherein the expression comprises expression of antisense RNA of NPK15 gene. Still a further means for recovering is expression of a protein inactivating the protein expressed by BC. The protein inactivating the protein expressed by the BC is for example Barstar protein, which inactivates Barnase nuclease by binding thereto. Still a further means for recovering is the expression of an enzyme producing the metabolite capable of compensating the deficiency resulted by the action of the BC. Still another means for recovering is the expression of an enzyme capable of converting a toxic substance or metabolite produced by the BC into a nonhazardous product. Such an example is provided by the enzyme, antibiotic phosphate transferase.

The present invention also describes a DNA construct for controlling transgene segregation and/or preventing the escape of a transgene into the environment. The DNA construct comprisesat least one BC containing at least one nucleotide sequence capable of blocking a molecular or physiological function of a transgenic host organism., The BC is closely linked to one or more nucleotide sequences or TGIs encoding desired gene products. The DNA construct further comprises one or more optional RCs capable of being externally regulated.

The BC comprises a DNA sequence, the expression of which blocks a molecular or physiological function of the molecular machinery of the host plant at the level of DNA, mRNA, protein or metabolite. The blocking results in death, phenotype alteration, untimely seed germination or flowering, incapability to form inflorescence, flowers or fruits, or other morphological change preventing free hybridization of the transgenic SRMO under natural conditions, hence, controlling the transgene spread through control on hybridization of the SRMO having the RBF.

The means for recovering comprises an optional RC and an external treatment or intervention step. This step further comprises an external compensation of a substance, a metabolite or hormone, repression of the promoter of the BC capable of silencing the blocking gene, mRNA expression by antisense RNA technique, expression of a protein capable of inactivating the protein encoded by the BC by specific binding or proteolysis or other protein-protein interaction, expression of enzyme capable of converting the toxic substance into a non-hazardous one, expression of the substance or metabolite capable of compensating or inactivating or interacting with the blocking toxic substance metabolite, as well as other molecular mechanisms which may be externally regulated.

The BC expresses in the host organism constitutively, or in an organ- or development-specific or in a spatiotemporal manner. The recovering occurs by external compensation of the blocking affected deficiency of a substance or by outside induction of a responsive recovering gene/protein or by a constitutive or temporal expression of the recovering gene.

The BC is closely linked to one or more TGIs. The BC is placed in the same chromosome as the TGI, preferably in the intron of the TGI.

The DNA construct according to the present invention may comprise at least the nucleotide sequences of two BCs, which are either similar to each other or different and they are situated on opposite sides of a TGI. The two-nucleotide sequences of the BC may form a double RBF system, and the BCs may be recoverable by the same or different means of recovery. According to the present disclosure the RC should be placed in the same SRMO individual as the BC, and preferably in a different chromosome. In a delayed RBF system, the BC and RC should be situated in different non-allelic chromosomes.

The BC can express an enzyme with unusual organ- or development-specificity. Such enzymes are L-asparaginase or L-glutaminase or an antisense mRNA of an enzyme essential for the development and/or functioning of the host organism, e.g. a nucleotide sequence encoding Ent-kaurene synthase A or a nuclease or nucleic aid recombinase.

The BC may comprise a nucleotide sequence encoding a protease or a toxin, e.g. Diphtheria toxin A or NPK15 protein kinase or an enzyme producing a toxic substance or metabolite e.g. an antibiotic.

The means for recovering the blocked function is provided by external application of a substance in order to compensate a deficiency of a substance caused by the BC. A preferred embodiment is providing gibberellins when the BC encodes for an antisense mRNA of ent-kaurene synthase A. Another preferred embodiment is expression of repressor peptide/protein binding the operon sequence, which controls the blocking gene expression. Example of this embodiment is a T10 tet repressor protein and tet-operator DNA sequence.

The RC comprises a nucleotide sequence providing an activating or a silencing mechanism of the expression of the BC. It comprises a nucleotide sequence, which is capable of expressing e.g. an antisense RNA of the blocking nucleotide sequence, wherein the nucleotide sequence of the RC expressing an antisense RNA is substantially similar to the NPK15 gene, or a nucleotide sequence capable of expressing a protein capable of inactivating the protein expressed by the BC. The inactivating protein is e.g. a Barstar protein which by binding to the Barnase nuclease inactivates it.

The RC may comprise a nucleotide sequence capable of expressing an enzyme producing a metabolite capable of compensating the deficiency resulting from the action of the BC. Alternatively, the RC comprises a nucleotide sequence capable of expressing an enzyme, which converts a toxic substance or metabolite produced by the BC into a non-hazardous product. Such an example is provided by the nucleotide sequence encoding an antibiotic phosphate transferase.

The DNA construct of the RC comprises for example a synthetic nucleotide sequence adapted to be inserted into the BC and the intron of another TGI. The intron of the TGI is adapted for the nucleotide sequence of the BC placed into the intron in opposite orientation to the TGI. An example of this is provided when inserting a nucleotide sequence substantially identical to the barnase gene sequence and having the SEQ ID NO:3.

The DNA construct of the RC according to the present invention is a synthetic sequence of barnase and barstar genes adapted for plant expression and comprising SEQ ID NO:1 and SEQ ID NO:2, respectively. Said DNA construct is further characterized by having a synthetic polycloning site, shown in SEQ ID NO:4 designed with an open reading frame adapted for B-galactosidase expression in a pUC19 cloning vector.

The present invention is related to vectors, and plasmids comprising one or more DNA constructs of the present invention and applied for mediating and/or transfer of said constructs or nucleotide sequences into SRMO.

The vectors, plasmids and cassettes may be transferred into cells of a SRMO forming transformed transgenic plant or animal cells or cell-lines, and ultimately transgenic plants or animals, the segregation and/or escape into the environment of which is controlled and prevented by the BC.

The present invention is related to molecular techniques controlling transgene escape in natural populations. The invention discloses a method of controlling the spread of a transgene during cultivation of transgenic SRMOs and release of the TGI into natural populations. For the convenience the method is described in detail only for plants.

In the practical use, transgenic plants carrying the RBF system may be grown in an open field and they do not differ from non-transgenic plants. Crop plants carrying RBF system require an external treatment to recover the blocked function usually at a particular stage of development. The method according to this invention is also applicable for animals particularly fish.

The RBF system is not only a particular molecular construct but in a broader sense a tool. The present invention operates with three concept constructs: TGI, BC and RC. The TGI is a DNA sequence, which is controlled by the RBF. It confers to the host organism some trait(s) useful for production purposes in agriculture, industry or in some other end use. The BC and RC are included in the RBF and they serve to control the TGI in transgenic SRMO. BC blocks a particular physiological or molecular function of the host plant preventing the sexual reproduction of plants carrying the TGI linked to the BC. The RC, if there is one, recovers the blocked function when an external treatment is applied RC does not work under natural conditions.

The BC and the TGI are linked together preferably closely. Because the BC controls the escape of the TGI, these two constructs should be linked together as close as possible to minimize or eliminate the possibility of crossing-over. The constructs should be located, at least, in the same chromosome and, at closest, the BC should be placed in the intron of the TGI.

The RC and the BC may locate close to each other or they may be in trans-position, even in different chromosomes depending on the RBF. In delayed RBF system, the RC should be in a different non-allelic chromosome than the one carrying the BC. When the recovering of the RBF comprises external compensation of a lacking metabolite, there is no need for a RC.

The RBF system leads to death, sterility or alteration of the phenotype of the transgenic SRMO. Being linked to the TGI, the RBF system prevents the transgene spread through hybridization. Hybrid SRMOs carrying a RBF system will die or will be incapable to propagate under natural conditions as a result of the action of the BC. When desired the SRMO can grow normally and propagate after the recovering mechanism is applied. Different RBF systems require different recovering mechanisms. The BC may be expressed constitutively or spatiotemporally (organ or development specifically). Expression of the RC may be constitutive or responsive to a particular outside stimulus.

RBF comprises a DNA construct linked to the TGI and encoding a factor capable to block a certain molecular or physiological function. This block leads to death or alteration of the phenotype or physiology of the transgenic SRMO further resulting in incapability to sexual reproduction. The BC may act through antisense mRNA, ribonuclease, toxin, hormone production, enzymatic action or another molecular mechanism. The block of a particular function could also be any alteration in the molecular machinery leading to some phenotypic or physiological changes preventing reproduction of the SRMO under natural conditions. It could be untimely seed germination or flowering, incapability to form inflorescence or fruits, formation of dwarf phenotype or some other morphological change. Several candidate constructs for the block of function are reviewed below.

Antisense technique may be used to block a key function of the plant by expressing antisense mRNA of the particular enzyme responsible for the key function. Antisense mRNA could block expression of particular gene(s) at a certain stage of development. For example blocking the expression of ent-kaurene synthase A of Arabidopsis leads to a dwarf phenotype of the plant (Sun and Kamiya, 1994, Plant Cell, 6: 1509–1518). Ent-kaurene is a key molecule in the biosynthetic pathway of gibberellins. Ent-kaurene synthase A is encoded by a single copy gene and may be blocked with antisense technique. If the antisense mRNA molecule is expressed at the germination stage, the lack of gibberellin may be compensated with an external application of GA3 (see the Example 2). Another example is antisense mRNA block of expression of glutamine synthetase in germinating seeds. The glutamine synthetase is a critical enzyme in all of the amino acid conversions in germinating seeds (Temple, et al., 1993, Mol. Gen. Genet. 236: 315–325).

Blocking the development of a SRMO may be achieved by expression of some enzymes originating from bacteria, e.g., L-asparaginase (Filpula, et al., 1988, Nucl. Acid Res. 16: 10385) or L-glutaminase (Ramakrishnan and Joseph, 1996. Canadian J. Microbiol. 42: 316–325), which can block nitrogen metabolism in the plant cell. The block on the biosynthesis of glutamine may be compensated by the external application of this amino acid (see Example No.1). The same technology may be applied in a range of other cases: blocking of auxin, cytokinin or ABA synthesis, production of amino acid(s) or other metabolite pathways.

U.S. Pat. No. 5,880,333 discloses a method for regulation of transgene expression through "receptor DNA cassettes" and chemical ligands activating the constructs. Several different types of unrecoverable blocks of function have been described by different groups in different patent applications and publications that are intended to provide control of escape of transgenic plants. Many of the molecular mechanisms described earlier are applicable in the present invention. For example unrecoverable block of embryo development is achieved in *Brassica napus* by expression of the modified exotoxin A of *Pseudomonas aeruginosa* under napin promoter (Koning et al. 1992, Plant Mol. Biol.,18:

247–258). Pollen sterility is achieved using diphtheria toxin A chain expression under lat52 promoter. Toxin expression may be applied to achieve cell ablation in developing pollen (Twell, 1995, Protoplasma, 187: 144–154). U.S. Pat. No. 5,498,533 describes regulation of potato development by expression of sense and antisense constructs of the calmodulin gene. Expression of sense-oriented calmodulin gene increased shoot and tuber growth, whereas plants carrying antisense constructs exhibit decreased shoot and tuber growth. Therefore, the expression of antisense calmodulin gene may be used as a factor blocking a physiological function.

There is a number of toxin or lethal genes, which are capable of blocking a certain function in the plant. Several nucleases destroy the mRNA synthesis machinery. The best-known nucleases are the Barnase and Ribonuclease A enzymes. Barnase originating from *Bacillus amyloliquefaciens* (Hartley, 1989, Trends Biochem. Sci. 14: 450–454) is the best known lethal gene since Mariani, et al. (1990, Nature 347, 737–741) used it for engineering fertility control in transgenic plants. The superior trait of the Barnase system is its specific inhibitor Barstar, which effectively blocks the RNAase action in plants (Mariani, et al., 1992, Nature, 357: 384–387). Thus, the lethal block of a function in plants achieved by the expression of barnase is recovered by the expression of the barstar gene.

Several catalytic or cytolytic lethal proteins can block certain functions. Ribosomal inhibitor protein (RIP) from saponin 6 RIP gene (Barthelemy, et al. 1993, J. Biol. Chem. 268: 6546548; GenBank ID SOSAPG, accession No. X15655) of Saponia directly interferes with the expression of proteins in a plant cell, without being toxic to other organisms. Widely reviewed in the art is the diphtheriatoxin A, which is another effective block. It has been used several times as a conditional lethal marker gene in plants (Czako and An, 1991, Plant Physiol. (Bethesda) 95:687–692; Nillson, et al., 1998, Plant J. 15: 799–804) because it leads to cell ablation (Van Der Geest, et al., 1996, Plant Physiol. (Rockville) 109: 1151–1158). Removal of the RIP or Diphtheria toxin A action is possible by an antisense technique; and there is also a report on effective inhibition of the diphtheria toxin by mansonone-D (Madhusoodana, et al., 1998, J. Cell. Physiol. 176: 40–49.). Mansonone-D, a sesquiterpenoid orthonaphthoquinone inhibited the cytotoxicity of ricin, Modeccin, *Pseudomonas* toxin and diphtheria toxin, can putatively be used for recovering the block effected by the expression of the toxins in plants. It has been shown that the *Pseudomonas aeruginosa* exotoxin A can specifically arrest tobacco embryo development (Koning, et al. 1992, Plant Mol. Biol. 18: 247–258).

There are still further examples for candidate genes in the art. U.S. Pat. No. 6,022,720 discloses the Bax protein that regulates programmed mammalian cell death. Harpin, the hrpN gene product of *Erwinia amylophlora* elicits HR in tobacco and is blocked by treatment with K52a, a protein kinase inhibitor (Popham, et al. 1995, Physiol. Mol. Plant Pathology, 47:39–50). NPK15, a tobacco protein-serine/threonine kinase acts as a suicide gene and blocks the proliferation of the host cells (Ito, et al. 1994, Mol. Gen. Genet. 245: 1–10). Genes from T-DNA of Agrobacteria responsible for overproduction of cytokinin or auxin have also been used for alteration of plant phenotype, i.e. ipt (Redig, et al., 1997, Physiol. Plantarum, 99: 89–96) oraux1 and aux2 gene (Beclin, et al. 1993, Transgenic Res. 2: 48–55; Hamza, et al. 1993, Theor. Appl. Gen. 86: 657–664). The above-mentioned genes were used as lethal markers or suicidal genes, but recovering the block of function has never been proposed. Several candidate genes may be used in the RBF system according to the present invention if the recovering of the block comprises an antisense technique or expression of the BC gene under a promoter repressible with the protein encoded by the RC.

Recovering the blocked function may be performed in a variety of ways depending on the particular model of the RBF system. For convenience the tools or means for recovering are divided into several groups as follows: external compensation of the blocked function, recovering by the repression of the action of a BC at the DNA level, recovering with antisense RNA technique, recovering on the protein-protein interaction level and on the enzymatic or another metabolite level.

External compensation of the blocked function may be used in case the RBF leads to a lack of a substance, metabolite or hormone. Lack of a substance or molecule may be compensated with external addition of the same or an analogous molecule e.g. with blocking of ent-kaurene synthase expression in germinating seeds (Example 2). Expression of L-asparaginase or L-glutaminase leads to lack of asparagine/glutamine (Temple, et al., 1993, Mol. Gen. Genet. 236: 315–325) but may be compensated by external addition of glutamine during the germination of seeds (Example 1).

Recovering by repression of action of the BC at the DNA level may be applied to any BC. The repression of the expression is affected by a particular DNA sequence having a boundary repressor element. A repressor element may be a protein, RNA or DNA. It may be any DNA sequence, the expression of which prevents the BC expression. The repressor molecule should be expressed from the RC placed under the control of an inducible promoter. For example, the known T10 tet repressor protein (Gatz and Quail, 1988, Proc. Natl. Acad. Sci. USA, 85: 1394–1397; Gatz, et al., 1991, Mol. Gen. Genet. 227: 229–237) may serve as a recovering element in the case the tet operon DNA sequence, which is responsible for binding to the repressor protein is situated inside the promoter of the BC (Example 4). The RC expressing the repressor protein may be integrated in another non-allelic chromosome and serve as a delayed RBF (Example 6).

Recovering with antisense RNA technique applies to most of the reported conditionally lethal marker genes acting as a RBF system recoverable by antisense technique. Expressed minus strand mRNA of the BC launches a silencing mechanism, which saves the host SRMO from the block of a certain function (Examples 4,6).

If the toxin protein has an inhibitor protein or enzymatically produced inhibitor metabolite, the recovering is provided at the protein level. The inhibitor may be a protein binding to the toxin or inactivating it proteolytically. The best-known example of this interaction is Barnase-Barstar mechanism (Examples 3, 5). The inhibitor, according to this invention, may be some enzymatically produced molecule being capable of inactivating the toxin impact For example, if the blocking factor is overproduction of a substance or metabolite, recovering can be an analogous molecule, which is able to block the enzyme overproducing the substance or metabolite.

If the toxin is a substance or metabolite produced by the enzyme encoded by the BC, the RC may be an enzyme inactivating the toxic substance. For instance, the blocking could be due to expression of an antibiotic and recovering the block could be achieved, for example, by the action of a specific phosphate transferase of this antibiotic.

Expression of RBF Systems Expression of the BC may be either constitutive or temporal with organ or development specificity. Expression of the RC may be responsive to an outside stimulus or the RC may be constitutively expressed as in a delayed RBF system.

Constitutive expression of the BC leads to the highest control of the transgene expression. The recovering mechanism is dependent on external treatment or stimulus. If the block involves a lack of a substance, metabolite or hormone, recovering of such a constitutively expressed block may be done by external compensation of the deficiency of the compound (Example 1). If the recovering comprises an expression of a product under an inducible promoter, the induction of the promoter also should be continuous. It means that an artificial recovering factor should be applied during the entire life cycle of the transgenic plant. Immediately after withdrawing the treatment, the plant will die because of the action of the BC.

Constitutive, as well as development- or organ-specific expression of both the BC and RC located in different non-allelic chromosomes, results in a delayed RBF, comprising the most convenient control of the transgene expression (Examples 5, 6). The most convenient way to construct this control is by double transformation. First, the constitutively expressing RC is transformed to the SRMO. Secondly, the construct containing the TGI linked to the BC is transformed in another non-allelic chromosome.

Transformants or their hybrids with non-transgenic plants are verified to have a single copy of the gene and it is also verified that the constructs are in different chromosomes. Homozygotes for both of the constructs are grown in the field. If the transgenic plant hybridizes with any other plant, the first hybrid progeny will survive, because all the plants will be heterozygous for both of the genes of the RBF. Beginning from the second hybrid generation, every second hybrid plant carrying the blocking gene will die, because the recovering and the blocking genes of RBF will segregate in different cells during meiosis. Thus, recovering of delayed RBF comprises the support of intraline crossing of the SRMO. The BC starts to work only in the second hybrid progeny, and leads to 50% negative selection of the transgene construct. One candidate constitutive expression promoter among others is for example 35S from CaMV (Condit, et al., 1983, J. Mol. Appl. Gen. (USA), 2: 301–314; Zaitlin, et al., 1985, Orlando, Fla. (USA). Academic press, 227–235; Williamson, et al., 1989, Plant Physiol., 90: 1570–1576), NOS (Depicker, et al., 1982, J. Mol. Appl. Gen. (USA), 1: 561–573), OCS (De Greve, et al., 1985 J. Mol. Appl. Gen.(USA), 1: 499–511). Candidate organ- or development-specific promoters may be chosen from a very wide group. For delayed RBF, it does not matter, if the promoter is "leaky" or not. It is important that both the BCs the RCs are expressed under the same kind of a promoter resulting in the expression of constructs concurrently in the same tissues of the host plant.

Organ, development and induction specific expression of the RBF genes leads to temporal control of critical stages in the life cycle of the transgenic plants and an external stimulus is needed to recover the block of a particular function. The developmental stages for temporal expression may be seed germination, flowering, embryo or fruit maturation, inflorescence formation, stem or root elongation and so on. Expression of the BC only at a particular stage of transgenic plant development makes the recovering procedure shorter and easier than in the case of constitutive expression (Examples 3, 4).

While expression of the BC should be regulated by an organ- or development-specific promoter, expression of the RC should be regulated by an inducible promoter, especially if the recovering is not based on external compensation of a lack of a particular metabolite. Thus, a crop plant carrying temporally expressed RBF needs artificial recovering only at a particular stage of development or in a particular organ. Without recovering, the plant will die or have an altered phenotype during that particular stage of development under natural conditions.

An important trait of the organ or development specific promoter is its high specificity excluding the case of delayed RBF. In other words, the promoter should be correctly expressing and not a "leaky" promoter, because the BC can kill or disturb plant development if expressed at undesirable stages.

Constitutive repression of the BC under natural conditions is a possible way to organize the RBF. If the BC is expressed at a particular stage of plant development under a specific promoter, the RC is under the control of a repressible promoter, e.g. modified 35Sp of CaMV or NOSp with TN10 tet repressor (Gatz and Quail, 1988, Proc. Natl. Acad. Sci. USA, 85: 1394–1397; Gatz, et al., 1991, Mol. Gen. Genet. 227: 229–237). The promoter is repressed through the life cycle with a protein expressed from a third gene situated under the constitutive promoter (Example 4). Promoter of the recovering element can be launched only when an outside stimulus (chemical or physical) removes the repressor element. In the case of the tet repressor, the binding protein changes its own conformation and activates the expression of the repressed construct in the presence of tetracycline. The recovering, in this case, is tetracycline treatment of the transgenic plant during expression of the BC. The other possible scenario is expression of all the three genes under the same organ-specific promoter. In this case, the T10 tet operon should be introduced in the promoter of the recovering gene. There are also other candidates for repressible promoters (Lanzer, et al., 1988, Proc. Natl. Acad. Sci. USA, 85: 8973–8977).

To construct RBF with temporal expression, organ and development specific promoters should be explored for possible expression of the BC. Several promoters show high seed germination specificity in expression. Unfortunately each promoter has also some additional 'star' expression at other stages of development. SH-EP or EP-C1 cysteine endopeptidases specifically degrade storage proteins. They are proteins highly expressed in germinating seeds. Additional expression may be observed in senescent tissues: cotyledons, pods and even in stems. These genes have large promoter regions of about 1200–1700 bp. EP-C1 cysteine endopeptidase has been cloned from *Phaseolus vulgaris* (Ogushi et al., 1992, Plant Mol. Biol. 19: 705–706) and expressed in a deletion analysis series in transgenic tobacco seedlings (Yamauchi et al., 1996, Plant Mol. Biol. 30: 321–329). Expression in matured pods makes the use of this promoter problematic for expression of the BC in germinating seeds.

SH-EP promoter of sulfhydril endopeptidase (1676 bp.) has been cloned from *Vigna mungo* (Akasofu et al., 1990, Nucl. Acid Res. 18: 1892) and investigated as SH-EP-cysteine endopeptidase (Yamauchi et al., 1996, Plant Mol. Biol. 30: 321–329). It expresses exclusively in the germinating seedlings. Only low additional expression has been detected in matured pods. Expression starts on the second day after germination is onset. The peak of the expression in germinating seeds occurs on the third day at the mRNA level and on the fourth day on protein level. Enzymatic activity continues until 5th–6th day and then fades. A cloned gene construction with its own promoter produces in transgenic tobacco even more protein than in *Vigna mungo*. Action of the promoter in the tobacco embryo was also found. Therefore, according to the present invention, this promoter may be used for the double RBF system during seed development and seed germination.

LEA promoters express at late embryo development stages (Hughes and Galau, 1989; Galau, et al., 1992, Plant Physiol. 99: 783–788; Devic, et al., 1996, Plant J. 9: 205–2015). LEA promoters are not "leaky" and are highly specific to late embryogenesis and consequently useful promoters for temporal expression of the RBF.

The promoter of the gene encoding for caffeic acid O-methyltransferase (COMT) enzyme expresses the protein highly specifically in the stem tissue of a perennial ryegrass *Lolium perenne* (McAlister, et al., 1998, Australian J. Plant Physiol. 25: 225–235). According to the present invention, expression of the BC under this kind of a promoter prevents inflorescence stem formation and, thus, propagation of the grass plants under natural conditions (Example 4).

A 620 bp promoter fragment from MT1-A (metallothionein-like) gene is sufficient to direct expression in transformed cotton roots (Hudspeth, et al., 1996, Plant Mol. Biol. 31: 701–705). According to the present invention, it can be used for blocking root development.

Malate synthase (MS) and isocitrate liase (ICL) promoters are active during germination and in seedlings, suppressed by sucrose, activated by GA3. Additional expression occurs in senescing organs and in germinating pollen. Cucumber (Reynolds and Smith, 1995, Plant Mol. Biol. 27: 487–497), oilseed rape (Zhang et al., 1994, Plant Physiol. 104: 875–864) and tomato (Janssen, 1995, Plant Physiol. 108: 1339) promoters have been well investigated in spatial and temporal manner in transgenic tobacco and oilseed rape. MS has a wider expression spectrum and is less ideal for germination specific expression (Sarah et al., 1996, Mol. Gen. Genet. 250: 153–161). The ICL and MS promoters are active in pollen and maybe used for the double RBF. MS and ICL promoters of *B. napus* have an average 1% activity in pollen in comparison with expression in seedlings (Zhang et al., 1994, Plant Physiol. 104: 857–864). These promoters express only slightly in senescing organs such as cotyledons (Graham et al., 1992, Plant Cell 4: 349–357). They may be activated in the dark and suppressed by sucrose, glucose and other sugars (Graham et al., 1994, Plant Cell 6: 761–772). Expression of ICL in mature seeds can achieve significant level (~5–10%) of expression in seedlings (Turley and Trelease, 1990, Plant Mol. Biol. 14: 137–146). MS and ICL promoters have been thoroughly investigated as cis-acting elements (Sarah et al. 1996, Mol. Gen. Genet. 250: 153–161).

A 17 bp fragment responsive to gibberellin from a promoter of catepsin B-like protein of wheat (Cejudo et al., 1992, Plant Mol. Biol. 20: 849–856) has been reported. AMY (high P1) -alpha-amylase is active in the endosperm during germination. All the known amylase promoters are also active in different organs of *Phaseolus vulgaris* and *Vigna mungo* plants (Minamikava et al., 1992, Plant Cell Physiol. 33: 253–258). There is a known GA3 induced P1 amylase from barley (Rahmatullah et al., 1989, Plant mol. Biol. 12: 119–121). Beta-1,3 glucanase is active in the endosperm during germination. This is an antifungal protein induced by GA4. It is active also in leaves and other organs, and is wound inducible (Vogeli-Lange et al., 1994, Plant J. 5: 273–278). There is a number of other candidate promoters for temporal expression and the number surely will increase every year.

Expression of the gene responsible for recovering the action of the BC requires promoters responsive to outside stimulus. The outside stimulus may be chemical or physical. Chemical stimulus may be any molecule capable of regulating the activity of a particular promoter. Physical stimulus may for example be temperature, osmosis, light, gravitation or something else.

The following two types of promoters serve as examples of responses to outside stimulus: salicylate and heat shock inducible promoters. Salicylate inducible promoters are involved in virus or other pathogen and stress responses. Promoter of the pathogenesis-related PA1a protein gene has been investigated in 5' deletion experiments in transgenic tobacco (Ohshima, et al., 1990, Plant Cell 2: 95–106). In another deletion experiment several regulatory elements have been found in a 902 bp PR-1a promoter (Van de Rhee, et al., 1990, Plan Mol. Biol. 21:451–461; Payne, et al., 1988, Plant Mol. Biol. 11: 89–94; Pfitzner, et al., 1988, Mol. Gen. Genet. 211: 290–295). Activity of the promoters rose after 24–48 hours of salicylate induction and was close to activity after a TMV infection. Heat shock promoters have been investigated in depth in different plants. Their activity was often several times higher than that of the 35S promoter. Induction of the HS promoters usually happened when ambient temperature rose to 35–45° C. (Ainley and Key, 1990, Plant Mol. Biol. 14: 949–967). A negative feature of the Heat Shock promoters is their expression in seedlings and their activation also by physical stimulus other than heat.

Chemically controlled expression of a promoter was reported in the invention "Control of the gene expression in plants by receptor mediated transactivation in the presence of a chemical ligand" (U.S. Pat. No. 5,880,333).

Tn10 tet repressor system (Gatz and Quail, 1988, Proc. Natl. Acad. Sci. USA, 85: 1394–1397) is activated by tetracycline, but its mechanism is opposite to a standard induction. This system requires two genes. First, the recovering gene under the promoter containing the tet operator. The second gene is positioned under a constitutive or organ/development responsive promoter gene encoding for the repressor protein binding tet operator DNA signal sequence. The system stays under repression until externally applied tetracycline activates the recovering gene.

Interrelation of the TGI, BC and RC

The invention operates with three concept constructs: (TGI), (BC) and (RC). TGI is a DNA sequence, which is controlled by the RBF. It confers to the host organism a trait(s) useful in agriculture, industrial production, forestry or horticulture. The BCs and RCs belong to the RBF and serve to control the TGI in transgenic plants. The BC blocks a particular physiological or molecular function of the host plant and prevents hybridization (proliferation) of plants carrying the TGI linked to the BC. RC (if there is one) recovers the blocked functions in case an external treatment is applied and it does not work under natural conditions.

The BC and the TGI are linked together. Because the BC controls the escape of the TGI, the constructs should be linked together as close as possible to minimize or eliminate the possibility of crossing-over. The construct should be situated, at least, in the same chromosome and, at closest, the BC can be situated in the intron of the TGI.

The RC and the BC may be placed close to each other or they may be in trans-position, even in different chromosomes depending on the actual RBF. When the recovering of the RBF comprises external compensation of a lack of a particular metabolite, there is no need for the RC. In the delayed RBF, the RC should be in a different non-allelic chromosome from the one carrying the BC.

Types of RBF

The RBF models can be divided in following types according to the mechanism of action and construction structure.

Externally compensated (simple) RBF

The RBF consists solely of the BC. The BC may be active constitutively (Example 1), development specifically (Example 2) or organ specifically. The recovering tool comprises external compensation of the required metabolite: amino acid (Example 1), hormone (Example 2) or some other metabolite. There is no RC in this embodiment.

Full RBF

RBF consists of both the BC and the RC. Expression of the BC may be constitutive or organ specific (Example 4). It may also be development specific (Example 3). RC can be responsive to an external physical (Example 3) or chemical (Example 4) stimulus.

Delayed RBF (Examples 5 and 6)

The BC and RC are positioned in different non-allelic chromosomes. Both of the constructs are in homozygous condition: BB (blocking construct) and RR (recovering construct). Expression of both of the constructs may be constitutive, organ specific or development specific. Preferably, both of the constructs are expressed under the same kind of a promoter. External regulation (artificial control) of the delayed RBF is performed by intraline crossing of the transgenic homozygous plants. Delayed RBF does not act in the first generation of outline hybridization because it will be in heterozygous condition BbRr (where 'b' and 'r' are recessive alleles which do not contain a BC or a RC respectively) and thus both of the constructs act as in a homozygous parental line. The RBF starts to act from the second outbreeding generation, when all the Bbrr hybrids will die or have an altered feature because of a lack of the recovering function. The RBF implies 50% negative selection of the TGI linked to the BC in each hybrid generation after the first hybrid progeny. The delayed RBF implies recognition of the fact that the RC can be released to the environment.

Reversed delayed RBF

Reversed delayed RBF (RD-RBF) controls the release of both the BC (linked to the TGI) and the RC. RC contains another blocking gene, which controls the release of the RC. The blocking gene action is recovered by a second RC, which is linked to a first BC and the TGI. Here we mark the construct alleles as follows: I-transgene of interest; B1-a first BC; B2-a second BC, which is different from the B1; R1-a first RC and; R2 -a second RC. B1 acts in pair with R1 and B2 acts in pair with R2. The alleles B1B1IIR2R2 are situated in one pair of the allelic chromosomes and R1R1B2B2 are situated in another pair of allelic chromosomes. The first out-hybrid will carry B1b1IiR2r2 and R1r1B2b2 genotype. Thus, starting from the second out-hybrid generation the blocking construct (B1) will control the release of the transgene of interest (I), and the blocking construct (B2) will control the release of the recovering construct (R1). Therefore, RD-RBF controls the release of all the transgenic constructs from the plant. External control (or artificial treatment) comprises the action of intraline crossing to support the homozygous condition of transgenic plants (as in ordinary delayed RBF). The second recovering or blocking construct can be fused with first blocking or recovering construct in the same gene sequences as follows: B1 fused with R2 and B2 fused with R1.

Double RBF

The RBF consists of two BCs. Preferably two different BCs are expressed under the control of different promoters to prevent the lack of the RBF action caused by a crossing-over, deletion of DNA, promoter silencing or other similar events. The blocking genes may be linked to the TGI from both sides of the construct or even inserted inside of the gene (FIG. 3).

Multiple RBF

Figure 8:
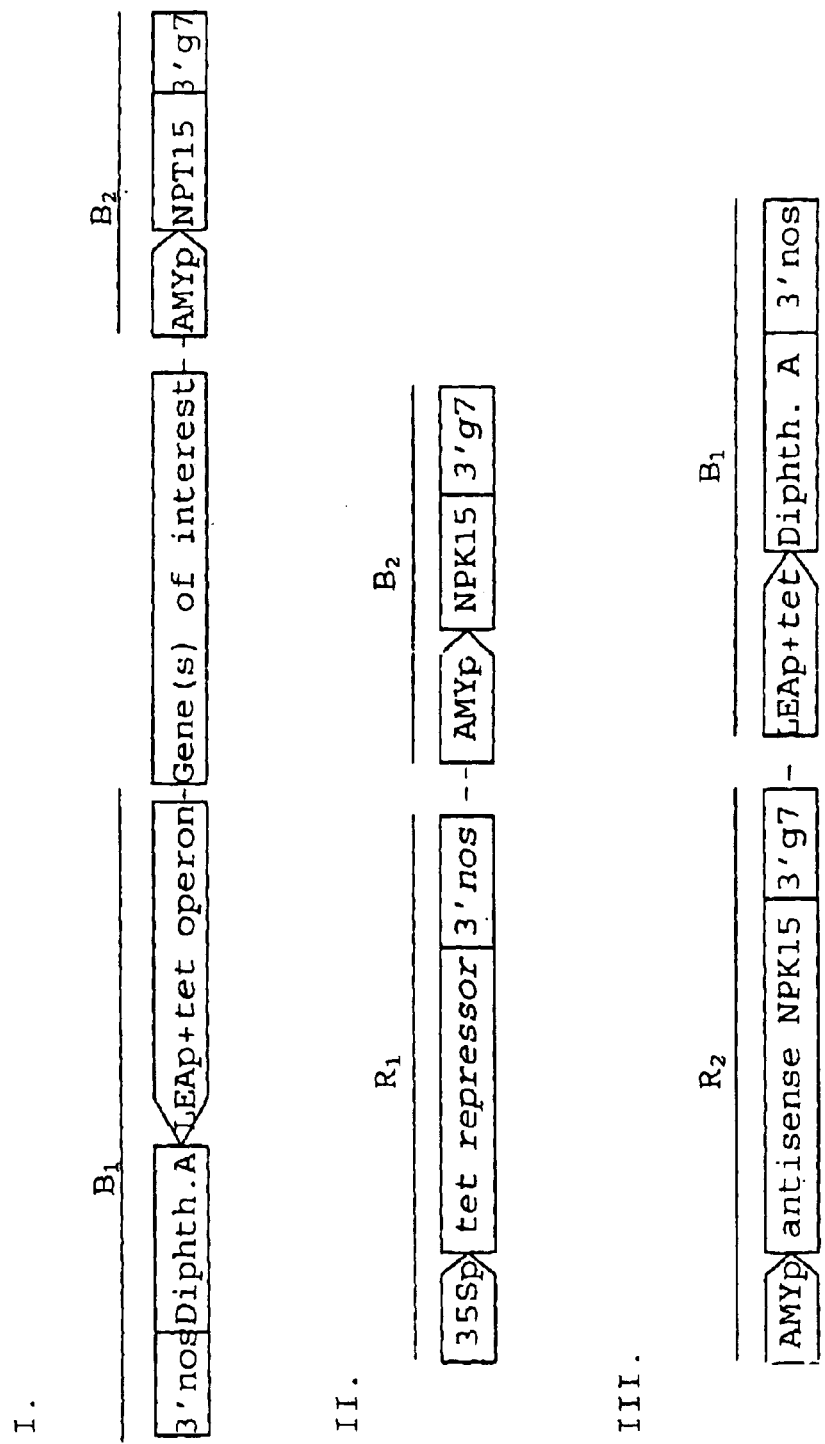

The triple RBF combines all the best traits of delayed, double and reversed RBF. It confers stronger negative selection than the delayed RBF. Triple RBF does not require special treatments besides intraline hybridization (as delayed RBF). It prevents any transgene construct flow into environment (as reversed RBF). It is double protected (as double RBF). It is quite easy to construct because different RBF genes are placed in three different transgenic insertions in different non-allelic chromosomes. The transgene of interest (I) is placed between two different blocking constructs (B1 and B2) in the same manner as in double RBF: B1IB2. Two different recovering constructs (R1 and R2) are placed separately in two different non-allelic chromosomes. Additional blocking constructs are linked to the recovering constructs in follow order: R1+B2 and R2+B1 Similarly as delayed RBF, the triple RBF also begins to work from the second hybrid progeny. Although, plants in progeny containing construct of the gene of interest and being able to sexual proliferation leave only 12,5% from whole hybrid progeny or 25% from hybrids carrying the transgene of interest. Schematically hybridization of the plants is shown in FIG. 8.

BC Inserted in the TGI

To minimize the possibility of separation of the BC and the TGI, the BC may be inserted in the intron of the TGI (Example 5). In this case, large mutations of the BC are almost impossible without destroying the TGI. Insertion of the barnase gene (blocking construct) in the intron of the TGI (uidA or GUS) in opposite orientation is shown in FIG. 3. Promoter of the BC coincides with the polyadenylation signal of the TGI. Second exon of uidA gene coincides with the 3' UTR of barnase. The coding sequence of barnase is located in the intron of the uidA gene. Polyadenylation signals of barnase coincide, partially, with the intron and, partially, with the exon of the uidA gene.

The following examples are meant to illustrate, but in no way to limit, the claimed invention.

EXAMPLE 1

Continuous compensation of a metabolite eliminated by constitutively expressing the blocking construct of L-asparaginase/L-glutaminase enzyme;

Recovery with externally applied L-asparagine/L-glutamine

Schematic positions of the genes are shown in FIG. 1A. The RBF works at the metabolite -amino acid -nitrogen metabolism level. It is the most controlled RBF system. Block of nitrogen metabolism leads to lethal effect resulting from the lack of amino acids, especially during seed germination. The L-asparaginase is active in sink tissues rich in asparagine. Expression of the enzyme in physiologically active tissues can inhibit normal nitrogen metabolism. The BC is placed close to the TGI or between TGIs. The L-asparaginase from *Lupinus angustifolius* (Dickson, et al., 1992, Plant Mol. Biol. 20: 333–336), *Erwinia chrysanthemi* (Filpula, et al., 1988, Nucl. Acid Res. 16: 10385), *Arabidopsis thaliana* (Casado, et al., 1995, Plant Physiol. 108: 1321–1322) or other source can be expressed under NOS, OCT, 35S or other constitutive promoters. Constitutive expression of the enzyme makes the host plant continuously dependent on external asparagine supply. Such a tight control of the transgene may be required when the TGI confers real threat to humans or the environment. The molecular constructs are described in FIG. 1A.

EXAMPLE 2

Antisense mRNA of ent-kaurene synthase A temporally expressed in germinating seeds of turnip rape Recovery with externally applied gibberellins Schematic positions of the genes are shown in FIG. 1B. The RBF works at the RNA silencing level with the recovery of the block on hormone level. Mutation in a single copy gene encoding for Ent-kaurene synthase A leads to dwarf phenotype of Arabidopsis thaliana. Expression of the antisense RNA of the enzyme leads to the same phenotype alteration due to the block of gibberellin synthesis in turnip rape. This is a temporal block of function because the enzyme is situated under the SH-EP (EP cysteine endopeptidase) promoter from Vigna mungo. The expression of the antisense ent-kaurene synthase starts during late embryogenesis and rises at the stage of seed germination. The host plant carrying the RBF develops dwarf phenotype and is incapable to reproduction under natural conditions. Recovering of this RBF comprises external application of gibberellins. It has been shown that normal plants were recovered from the dwarf phenotype of Arabidopsis by external application of gibberellins (Xu, et al., 1997, Plant Physiol. (Rockville) 114: 1471–1476; Phillips and Huttly, 1994, Plant Mol. Biol. 24: 603–615). In the practical use, seeds of the transgenic crop plants should be coated with a gibberellin containing mix in order to obtain plants with a normal phenotype. The molecular construct is shown in FIG. 1B.

EXAMPLE 3

RBF with barnase controlled by SH-EP endopeptidase promoter;

Recovery by barstar gene controlled by HS heat shock promoter

Schematic positions of the genes are shown in FIG. 4. The RBF works at the protein interaction level. It consists of barnase and barstar genes originating from Bacillus amyloliquefaciens (Hartley, 1989, Trends Biochem. Sci. 14: 450–454). Barnase is the best-known lethal gene since Mariani, et al. (1990, Nature 347, 737–741) used it for engineering fertility control in transgenic plants. When expressed in the plant Barnase blocks the expression of all the genes through destroying RNA molecules. Acting as the BC the barnase gene was expressed under cysteine endopeptidase promoter (SH-EPp) cloned from Vigna mungo and, at first, described as sulfhydryl-endopeptidase promoter (Akasofu et al., 1990, Nucl. Acid Res. 18: 1892; Yamauchi et al., 1996, Plant Mol. Biol. 30: 321–329). The RC comprises barstar gene placed under heat shock promoter (HSp) of soybean (Ainley and Key, 1990, Plant Mol. Biol. 14: 949–967). The barnase was placed under the SH-EP promoter and allowed to express during embryogenesis and seed germination in transformed tobacco plants. The schematic structure of the construct carrying four genes is shown in FIG. 4. The DNA construct contains also uidA (GUS) as representative of the gene of interest and hpt gene as a selectable marker. The uidA gene was cloned under 35S promoter of CaMV and the hpt gene under NOS promoter of Agrobacterium. All four genes were situated in one T-DNA of pBIN19 (pGPTV-HPT) based vector (Bevan M., 1984, Nucl. Acid Res. 12: 871–8717; Frish et al., 1995, Plant Mol. Biol. 27: 405–409).

To explore expression of the HSp and SH-EPp we transformed tobacco plants with the uidA gene drown under the promoters. Investigations of the transgenic tobacco plants showed that HS promoter expressed leaky GUS enzyme sometimes at the low level in generative organs. It forms a slight peak of expression on the third day of germination and fades during the next few days without outside stimulation. It activates in response to a high temperature in the range of +37–45° C. applied for 0.5 to 3 hours. For HS promoter the activation of 1 hour +40° C. treatment was used. The GUS expression under HS promoter rose during the first two days and continued for at least 3–4 days after the heat shock. SH-EP promoter expressed GUS enzyme in the embryo and in the seedlings. Peak of GUS activity under SH-EPp was achieved at middle tolate stages of embryo development and again appeared on the third to—fifth days of germination. There was no expression of SH-EP promoter in other organs of tobacco plants.

Several transgenic tobacco plants were recovered after transformation by the DNA construct containing the uidA gene of interest, hpt selectable marker gene and the RBF with barnase and barstar genes. The transgenic tobacco plants carrying the RBF construct showed normal phenotype: they grew, flowered and produced seedpods after self-pollination normally. The seeds from the plants were of normal size, however, they did not germinate. Heat shock application during germination does not recover the blocked germination function of the transgenic seeds. As we predicted, the embryo development was arrested by the expression of Barnase at the time of pod maturation. Therefore, embryos of the seeds were, actually, dead.

All the inflorescences were cut off from the tobacco plants, after which tobacco plants were allowed to form inflorescences again. The plants with new flowers and green seedpods were exposed to heat shock +40° C. for 1 hour every second day. Matured seedpods were collected from the tobacco plants. The seeds were germinated and heat shock was applied at least one time for one hour +40° C. on the second or third day of germination. The heat-treated seeds formed normal seedlings, which grew in normal tobacco plants. The seeds started to germinate also without heat shock. Most of them, however, could not expand their cotyledons. They exhibited etiolated phenotype and died. Part of the seedlings, however, expanded cotyledons and overcame the block of development. Most evidently, the successfully germinated seeds have accumulated substantial quantity of Barstar protein to inhibit action of Barnase expressed during seed germination. Only repeated heat shock treatment of plants carrying seedpods removed the block of germination function of seeds. One time 2 hours +40° C. heat shock applied at different stages of embryogenesis from flowering to seedpod browning did not remove the blocked germination. Continuous heat shock applied to tobacco plants with seedpods and flowers neiter had any success. The seedpods suffered from drought and seeds could not developed properly. While control non-transgenic seeds germinated after the continuous heat shock, the RBF carrying seeds did not germinate. Perhaps, the continuous heat shock dried the seedpods, and HS promoter did produce enough Barnase in time before the seedpods dried. While part of the F1 germinated transgenic seedlings were not positive in GUS assay as a result of the transgene segregation, all the seeds of same transgenic line not treated with heat shock did not germinate. It can be explained by fact that GUS expression driven by SH-EP promoter was registered at low level also in other parts of seedpod. It means that Barnase could block mRNA synthesis in the embryos, which did not carry the RBF.

Figure 5A:
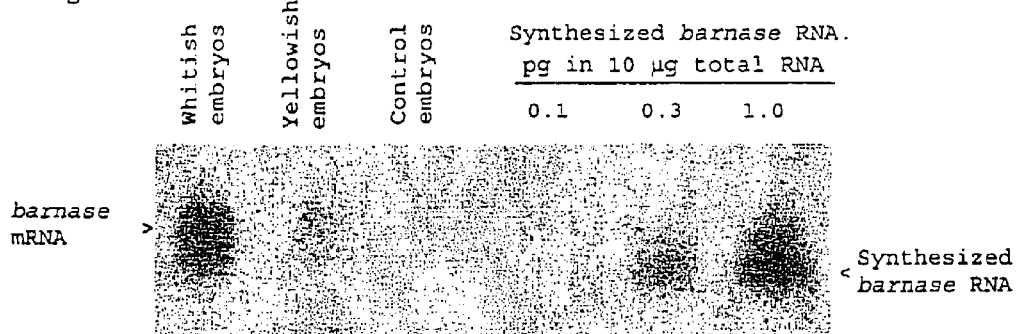
FIGS. 5A–5C depicts expression of blocking (barnase) and recovering (barstar) genes of the RBF described in Example 3 and FIG. 4 during embryo maturation, seed germination and with/without heat shock treatment showed on the level of mRNA (Northern analysis).
Figure 5B:
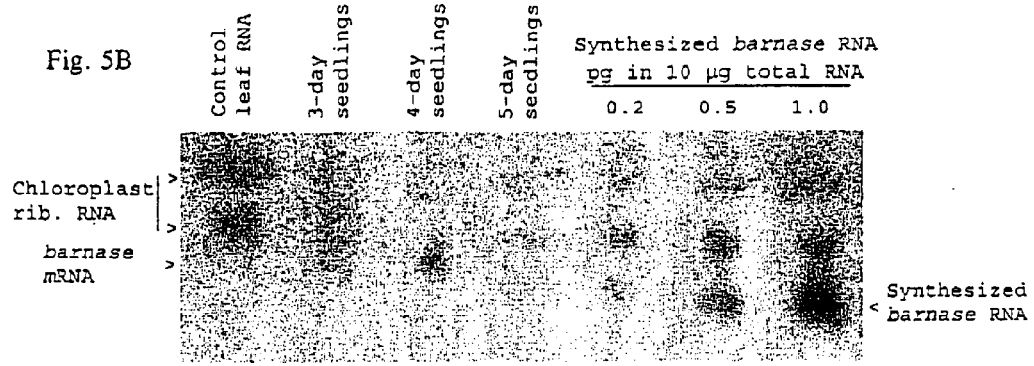
Figure 5C:
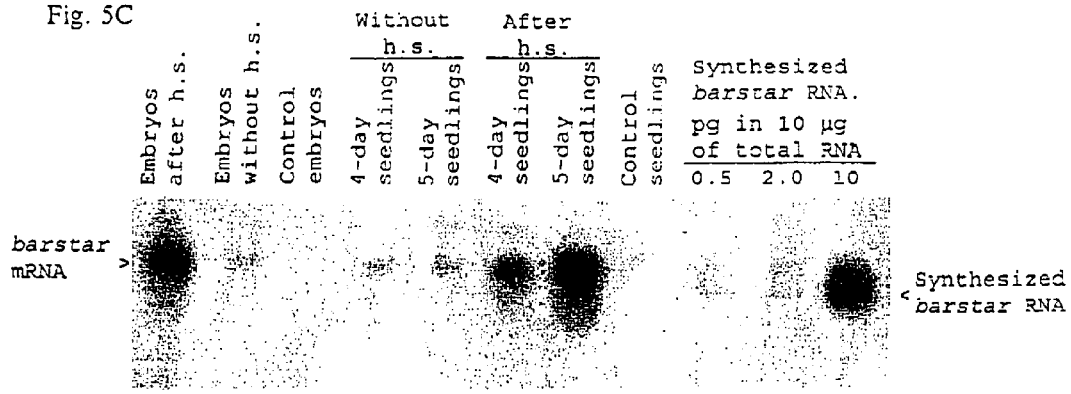

Action of the BC and RC was confirmed in Northern expression analysis (FIG. 5). The barnase mRNA expression under SH-EP promoter had peak at the stage of middle embryogenesis (whitish embryos) at the level 0.1 pg/1 aeg of total RNA and decrease to 0.03 pg/µg of total RNA in the late embryogenesis (yellowish embryos). Second peak of the expression started from third day of seed germination, achieved 0.04 pg/1 aeg of total RNA at the forth day and disappeared to fifth day of germination. HS promoter expressed barstar mRNA leaky at the both stages of development: embryo and seed germination at the level 0.05 0.2 pg/µg of total RNA. The high temperature treatment activates the barstar expression under HS promoter up to 13 pg/µg of total RNA. Especially, HS promoter activity rose after several subsequent high temperature treatments each given on one or two subsequent days. Although, Northern analysis showed that HS promoter has high leaky activity, barstar expression is not enough to inhibit barnase action without high temperature treatment, especially at the stage of embryogenesis. In general, when keeping in mind that protein expression often follows the mRNA expression with some hours up to one day delay, the results of Northern and GUS analysis of expression of SH-EP and HS promoters was comparable and the RBF construct worked as it was predicted.

Practically, recovering of the RBF comprises an application of 1-hour +40° C. heat shock once in two days during seedpod development and at least one time during germination. Any other used temperature treatments could not remove the blocked seed germination. The RBF reliably controls the segregation and escape of the gene of interest (uidA). If even occasionally the transgenic plants would be heated at the same manner in nature, it could not be repeated in several growing seasons. The transgenic plants producing seed can be grown in greenhouse conditions, where heat shock is easy to perform. In the open field the transgenic plant carrying the RBF produces seeds, which do not germinate. Pollen carrying the RBF can pollinate outside relative plants. The seeds produced after the pollination, however, do not germinate. Therefore, the RBF prevent transgene spread in natural environment.

A single RBF system comprises solely a BC and the action is compensated by external application of the recovering means. In a general or full RBF is activated in response to an outside stimulus and releases a function arrested by the BC expressed under a different promoter. In a delayed RBF RC is placed in a different non-allelic chromosome. The reversed delayed RBF (RD-RBF) system comprises two different RBFs which are situated in different non-allelic chromosomes opposite to each other so that the BC of the first RBF is linked to a RC of the second RBF system and the BC of the second RBF system is linked to the RC of the first RBF system.

EXAMPLE 4

NPK15 gene expression in ryegrass stem

Recovery with antisense sequence of the gene placed under hybrid NOS promoter regulated with T10 tet repressor.

The schematic positions of the genes are shown in the FIG. 1C. The RBF operates through cell ablation resulting from the toxin expression with recovery by the antisense-RNA silencing. The BC encoding for NPK15 gene (Ito, et al., 1994, Mol. Gen. Genet. 245: 1–10) causes death of the plant. The promoter of gene encoding for caffeic acid O-methyltransferase (COMT) enzyme expresses a protein product high specifically in stem tissue of a perennial ryegrass Lolium perenne (McAlister, et al., 1998, Australian J. Plant Physiol. 25: 225–235). The host ryegrass expressing the RBF grows normally. It is however, incapable to form a stem or an inflorescence. The RBF prevents any possibility of crossing of the transgenic ryegrass and makes the plant more attractive in use as a forage crop. The stem formation and seed production is possible only when the planting seed has been treated with tetracycline. The RC consists of two genes. The first gene encoding for the T10 tet repressor protein is constitutively expressed under 35S promoter from CaMV. The second gene encoding for the antisense DNA sequence of the gene encoding for the NPK15 is expressed under a chimeric NOS promoter containing tet operon sequence repressible by the repressor protein. Tetracycline spray in the field removes the repression from the promoter of the antisense harpin gene and launches a silencing mechanism in the stem of the ryegrass. The BC and RC may also be for example barnase and barstar genes.

EXAMPLE 5

Delayed RBF, when the BC, barnase, is located under an organ specific promoter in the intron of the TGI.

RC is the barstar gene situated in a different non-allelic chromosome under the same promoter.

Schematic positions of the genes are shown in FIG. 2A. The RBF operates at the protein—protein interaction level. The BC barnase is situated in the intron of the TGI uidA (GUS) to prevent separation of the BC and the TGI and thereby preventing crossing-overas well. The barnase gene is regulated by SH-EP promoter from Vigna mungo. The RC, barstar, is situated in a different non-allelic chromosome under the same promoter. The transgenic plant does not differ from the non-transgenic one because of the continuous inhibition of Barnase by Barstar. Recovery of the transgenic plants is provided when the homozygous (BBRR) transgenic plants cross with each other and the homozygous genotype is thus supported in the progeny. When the transgenic plant crosses with an outside plant, the hybrid plant of the first generation also exhibits normal phenotype but carries the heterozygous (BbRr) genotype. Delayed RBF becomes effective from the second hybrid generation, when the BC and the RCs will segregate into different host cells. Every second hybrid embryo containing a BC will carry the Bbrr genotype leading to death of the plant during embryogenesis or germination, the stage depending on the plant species. Thereby the BC causes strong negative selection during hybridization with outside plants. This negative selection will eliminate the transgene from the population during several generations. The number of the plants carrying the negative selection factor (X) will be reduced with the number of generations (n) in the following proportion: $X=Y.2^{-n}$, where Y is the starting number of the plants carrying negative selection in a big population. For example, if the starting number of the hybrid plants was Y=1000, after n=10 generations the number of plants X carrying RBF drops below 1, $X=1000.2^{-10}$ or X<1. Because the BC is situated inside the TGI, crossing-over cannot separate the TGIt and the BC into allelic chromosomes.

The sequences of the intron and the polyadenylation signal of the gene of interest (uidA) contemplated with the promoter, UTR, coding sequence and polyadenylation signal of the blocking gene (barnase). The signal sequences of the intron used in the construct: TA proportion 55–70%, 5' exon/intron boundary site AG/GUAUGU (SEQ ID NO:5), branch point sequence (UA)CUAAC (SEQ ID NO:6)

located 20–50 nt upstream from the 3' intron/exon boundary site GCAG/G (SEQ ID NO:7). U-rich sequences stimulate splicing regardless of their position within an intron. Single or double U-to-G substitutions strongly inhibit splicing. High content of AU and especially U is required in the first and last 50 nts of the intron. Exons are about 15% richer in GC content than introns.

Termination of transcription by RNA polymerase II requires the presence of a functional polyadenylation signal in transcription unit near the upstream element (NUE) AAUAAA (SEQ ID NO:8). Plants however, have many modifications of this site. The far upstream element (FUE) is even more unconserved. Common traits of FUEs are U- or UG-rich sequences situated 10–40 nts before NUE. The most often occurred is UUUGUA (SEQ ID NO:9):but also UGUGUUUUUU (SEQ ID NO:10) or UGUUGUG(SEQ ID NO:11). The cleavage site is also not highly conserved. Usually it consists of Y A nucleotides and is positioned 10–30 nts after the NUE site.

In the promoter region, there are two distinct boxes: TATA in consensus sequence TCACTATATATAG (SEQ ID NO:12) located 15–60 nucleotides from the start of the transcription and CAAT (SEQ ID NO:13) or AGGA (SEQ ID NO:14) box located 30–100 nucleotides upstream the TATA box. Translation starts 40–80 nt downstream from the start of the translation from the AUG codon in preferred sequence AACAA TGGCT (SEQ ID NO:15) (nucleotides in bold are highly conserved). As an example, the sequence of barnase gene situated in the intron of uidA gene under SH-EP promoter is shown in FIG. 3.

EXAMPLE 6

Delayed double RBF

Single recovering

Delayed double RBF with a single RC, when the BC are barnase situated under the chimeric AMY promoter containing the T10 tet operon sequence and NPK15 gene situated under the AMY promoter:

The RCs are encoding for tet repressor protein gene joined with antisense barnase in 3' UTR expressed under AMY promoter and situated in different non-allelic chromosomes.

Schematic positions of the genes are shown in FIG. 2B. The first BC encoding for the NPK15 is situated under the control of chimeric AMY promoter carrying the tet operon. Repressor protein constitutively produced from the RC binds to the operon and represses the NPK15 toxin production. The BC starts to act from the second hybrid progeny, when the RC segregates in different generative cells. The second blocking gene barnase is repressed by a silencing mechanism launched by the expression of antisense RNA from the same recovering gene. Double RBF practically eliminates the possibility to break the RBF without disruption of the TGI(s). If we accept an average frequency of mutagenesis as 10-9, the frequency in the double RBF breaking will be $10^{-9}(10^{-9}$, or, practically, 0). AMY promoter is from the host plant and is identical to the plant's own promoter. In the case of failure of the RBF by silencing the AMY promoter, the function of the amylase enzyme of the plant will also be destroyed. The selection marker gene nptII is situated between two Cre recombinase signal sites. The selective marker transformed with the RC can be excised from the transgenic plants during the second transformation by Cre recombinase encoded by the cre gene (Gleave, et al., 1999, Plant Mol. Biol. 40: 223–235) linked to the BC. Alternatively, transformation with the Cre recombinase can be performed separately before the transformation with the BC. Then the cre construct can be selected off from plants carrying the RC, and nptII-free plants can be transformed with the BCt linked to the TGI. Thus, a freely hybridizing RC will contain only the barstar gene, which has no selective or physiological effect on relative weed or hybrid plants.

EXAMPLE 7

Triple RBF

Schematical positions of the genes are shown in FIG. 8. The first RBF consists of Diphtheria toxin A blocking gene (El) driven under chimeric LEA promoter with inserted tet operon sequence, and recovering gene (R1) encoding Tet10 repressor protein and driven under 35S promoter from CaMV. The second RBF consists of NPK15 blocking gene (B2) driven under Amy promoter, and recovering gene (R2) encoding for antisense NPK15 and driven under the same Amy promoter. The transgenic plant carries three different transgenic constructs situated in different non-allelic chromosomes. The first construct contains a gene of interest (I) placed between two different blocking constructs (B1 and B2). The second construct contains afirst recovering construct (R1) linked to the second blocking construct (B2). The third construct contains a second recovering construct (R2) linked to the first blocking construct (B1). The first RBF consisting of B1 and R1 constructs acts in the stage of late embryogenesis. The second RBF consisting of B2 and R2 acts mainly at the stage of seed germination. The segregation of the constructs during hybridization and interbreeding is shown and described in more detail in FIG. 9.

Conclusive Review of the Examples

The above analysis of the examples enables the comparison of the candidate constructs and mechanisms on the range, reliability and convenience of the various RBF systems in controlling gene segregation and escape. The superiority of the RBF rests in the ability to eliminate the BC action with simultaneous action of the TGI. In plants the block can fail to operate following crossing-over or mutations of the BC, or through a silencing mechanism. Crossing-over can separate the BC and the TGI in case the genotype of the host plants is heterozygous for those genes. The closer together the BC and the TGI(s) are, the smaller is the possibility of separation of the constructs. Positioning of the BC in the intron of the TGI sufficiently decreases the possibility of separation or mutation of the BC without damage to the TGI, because of coinciding of signal and coding sequences of both of the genes. Constitutive expression of the BC may lead to continuous pressure to break of the block. Therefore, it is preferable that the BC is expressed under organ- or development-specific promoters. Delayed RBF increases the possibility of the separation or separate repression of the BC and the TGI, because of several hybridizations with other plants. The case of two different BC on both sides of the TGI(s) (double RBF) decreases drastically the possibility of failure of the blocking. Use of these precautionary means eliminates the possibility of functional failure in the BC(s).

The efficiency of the BC is also important. Thus, antisense RNA BC do not look secure enough, because the silencing mechanism is not entirely sure. In contrast, recovery with antisense RNA expression is an appropriate tool, because insufficiently silenced BC just kills the host plant. Some toxin or hormone overexpression may also be insufficient to alter plant phenotype dramatically enough. The Barstar- Barnase pair is the most reliable working system many times verified in plants. NPT15 phytotoxin has also been shown to be effective as a plant 'suicide' gene.

Convenience in the use of the RBF is important in plant production. The most inconvenient type of RBF is the one needing a continuous supply of the plants by a metabolite, which the plant is lacking, or continuous induction of the RC. Short or one step treatment like organ- or development-specific expression of the BC is more preferable. It can be performed, for example, as coating of seeds with the inducing or compensating chemical or as a temperature treatment of the seeds or parental plants. Delayed RBF is the most convenient in use. It does not require any special treatment of the plants besides intraline hybridization to support the homozygous genotype of RBF.

There are well known impacts of hazardous substances in plant and animal health. Exact development- or organ-specific expression may eliminate the possibility of risks to the consumers if the expression of the toxin does not occursin consumable tissues. RNAses (Barnase) are not toxic to humans and animals, because RNAase is the enzyme, which is abundantly present in the cells of humans or animals. There are no risks associated with natural plant hormones or metabolites or antisense RNA. There is also no effect on plants, animals or humans from the Barstar boundary protein. It is important for delayed (most convenient) RBF, because the RC spreads freely in natural populations (besides RD-RBF). Spread of the RC can be accepted only in the case the RC is a molecule, which has not effect on plants or other organisms. Such RCs can be antisense RNA of any blocking gene, Barnase or boundary protein of T10 tet operon. The selective marker gene should be removed from the RC of the delayed RBF. It can be performed by Cre recombinase or transformation of the plant with a double T-region containing vector.

RD-RBF (reversed delayed RBF) controls segregation and escape of both the TGI and the RC. The RC is controlled with another (second) RBF situated opposite to the first RBF. Thus, in this model there is no transgene construct capable of escaping into the environment.

The multiple or triple RBF combines all the best traits of delayed, double and reversed RBF. It confers stronger negative selection as the delayed RBF. Triple RBF does not require special treatments besides intraline hybridization (as delayed RBF). It prevents any transgene construct flow into environment (as reversed RBF). It is double protected (as double RBF). It is quite easy to construct because different RBF genes are placed in three different transgenic insertions in different non-allelic chromosomes.

To summarize the reviewed models, the most convenient, sure and save RBF (besides the case when the RBF performs an additional function) is the delayed double RBF with single RC and removed selectable marker or double RD-RBF. It is preferable that the genes of the RBF should be expressed under the same type of a promoter, which is the plant's own promoter expressing an important plant enzyme, e.g., cysteine endopeptidase. The use of such a promoter prevents silencing of the ones in the transgenic plant. The BCs, preferably, should be different in function, e.g. NPK15 and barnase, or expressed in different organs or stages of development. They should be placed on both sides of the TGI(s). It is preferable to place one of the genes in the intron of the TGI. The RC can be a single gene expressing the hybrid antisense RNA for both of the BCs. In the case the RC freely distributes itself through hybridization, it should be absolutely neutral in nature. It can be achieved, if the selectable marker will be removed and antisense RNA of the rRC does not contain 5' and 3' parts of coding sequences of the BCs. Such a RC would contain just plant is own promoter and RNA coding sequence being absolutely nonsense for the plant.

Detailed Description of the Drawings

FIG. 1A–1D. The molecular constructs described in the Examples 1, 2 and 4 are shown. The constructs are drawn schematically to show the principle disposition of the genes. Abbreviations: p-promoter, 3 or polyA-3 end of the gene (polyadenylation site). Boxes of promoters show the direction of the gene sequences.

FIG. 2A–2D. The molecular constructs described in the Examples 4–5 are presented. The constructs are drawn to show the principle disposition of the genes. Abbreviations: p-promoter, 3 or polyA-3 end of the gene (polyadenylation site), Cre-signal site for Cre recombinase. Boxes of promoters show the direction of the gene sequences.

FIG. 3. Sequence of the barnase gene placed inside the intron of the uidA gene: The barnase gene construct is shown downstream and contains the SH-EP promoter (about last three hundred nucleotides are shown) coding sequence and polyadenylation signal sites. The uidA gene construct is placed upstream beginning from the 1735 nucleotide of the coding sequence. The uidA gene construct contains exon intron exon polyadenylation site sequences. Abbreviations: nt nucleotides; FUE far upstream element of polyadenylation site; NUE near upstream element of polyadenylation site; SphI, SpeI, PstI, BclI restriction sites; >, <-direction of the signal sites, CAAT and TATA signal boxes of the promoter.

FIG. 4. The molecular construct described in the example 3 is shown. The construct is drawn schematically to show the principle disposition of the genes. The abbreviations are p-promoter, 3 or polyA-3 end of the gene (polyadenylation site). Boxes of promoters show the direction of the gene sequences. The action of RBF genes is described below the blocking and recovering constructs.

FIGS. 5A–5D. Expression of the BC (barnase) and the RC (barstar) of the RBF described in Example 3 (FIG. 4) during embryo maturation, seed germination and with/without heat shock treatment showed on the level of mRNA (Northern analysis).

A. Expression of barnase mRNA in tobacco embryos at the stages of middle (whitish embryos) and late (yellowish embryos) embryogenesis. 10 $\mu$g of total RNA was loaded in each lane. As controls non-transgenic embryos total RNA and 0.1–0.3–1.0 pg of synthesized barnase RNA mixed with 10 aeg of total non-transformed tobacco embryo RNA were used. Barnase mRNA expressed in middle embryogenesis 0.1 pg/$\mu$g of total RNA and 0.03 pg/$\mu$g of total RNA in late embryogenesis.

B. Expression of barnase mRNA in tobacco seedlings. 10 $\mu$g of total RNA was loaded in each lane. As controls non-transgenic leaf total RNA and 0.2–0.5–1.0 pg of synthesized barnase RNA mixed with 10 $\mu$g of total non-transformed tobacco leaf RNA were used. Expression of barnase mRNA started on the third day of germination, achieved a maximum 0.04 pg/$\mu$g of total RNA on the forth day and faded to fifth day of germination. Two non-specific bands of chloroplast ribosomal RNA were also detected on the blot.

C. Expression of barstar mRNA after heat shock (h.s.) and without heat shock (h.s.). 10 $\mu$g of total RNA was loaded in each lane. 0.5–2.0–10 pg of synthesized barstar RNA mixed with 10 μg of non-transgenic control tobacco embryos RNA were used as positive control. Heat shock treatment activated barnase mRNA expression up to 13 pg/μg of total RNA in both the embryogenesis and germination stages of the development. The HSp expressed leaky barstar mRNA without temperature treatment at the level 0.05 0.2 pg/μg of total RNA.

Figure 6:
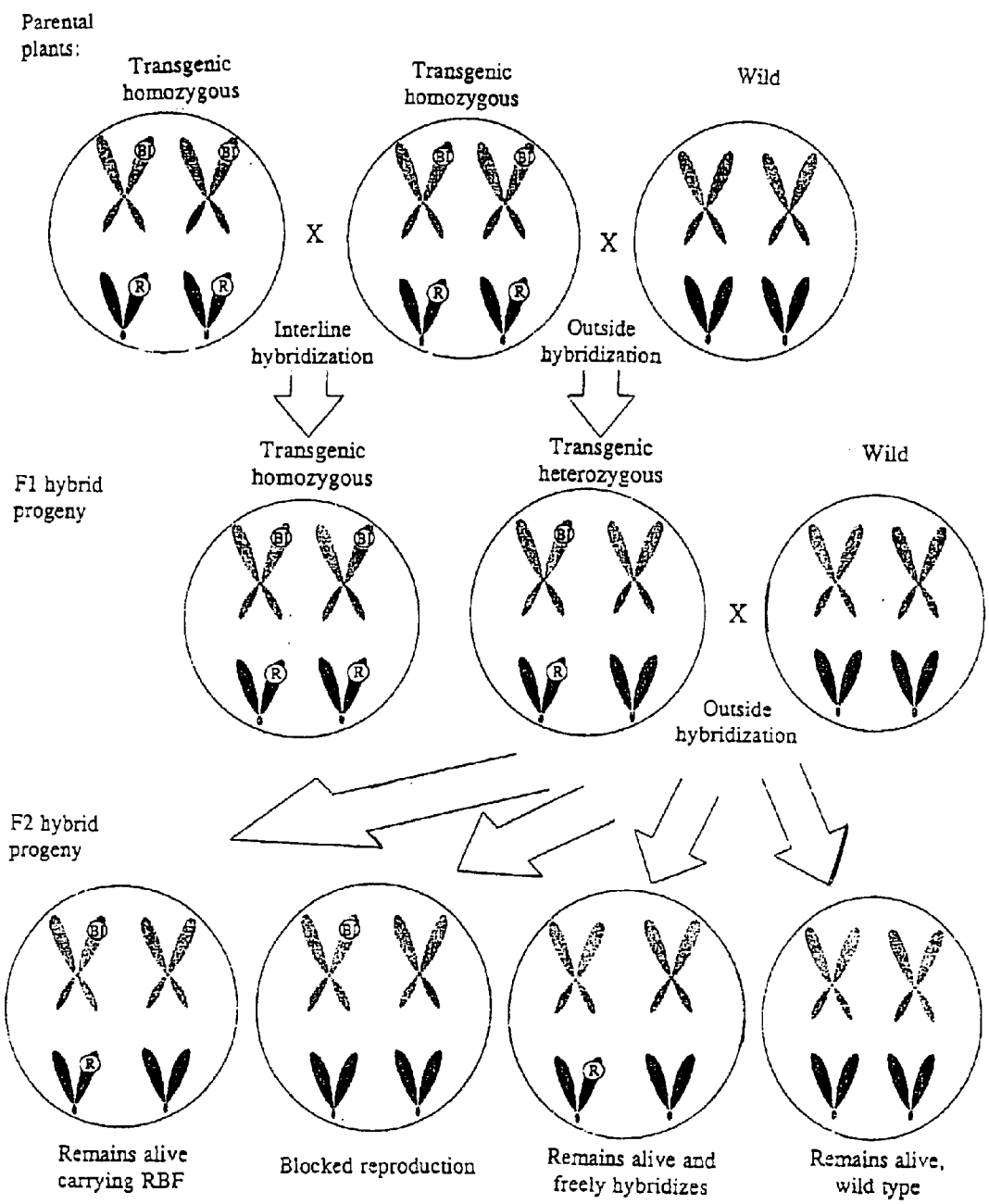
FIG. 6 depicts schematically hybridization of transgenic plants carrying a delayed RBF construct.

FIG. 6. Schematic hybridization of transgenic plants carrying delayed RBF construct. Condition of chromosomes carrying blocking construct (B) linked to gene of interest (I) as well as placed in different non-allelic chromosome recovering construct (R) are shown in circles representative a plant genome. Wild type chromosomes are shown without spots marking BI or R. The parental plants included in hybridization are shown in the first line. As it can be seen, the condition of genes involved in the RBF does not change in the result of intraline hybridization. Intraline F1 hybrid progeny keeps the homozygous genotype of RBF and the gene of interest. External regulation of the RBF implies to support homozygous condition of the transgenes through intraline hybridization. In the case of outside hybridization, the first F1 hybrid progeny genotypes are heterozygous for all transgene constructs. The plants remain alive. The delayed RBF starts to act from the second F2 hybrid progeny in the case of outside hybridization. From the F2 outside hybrids, only half of the plants carry blocking construct (B) linked to the transgene of interest (I). Half of them will be unable to reproduction because of absence of RC. Therefore, beginning from the second outside hybrid progeny, 50% negative selection eliminates the transgene of interest from natural populations. In the case of delayed RBF, RC can freely segregate in the genomes of wild population plants.

Figure 7:
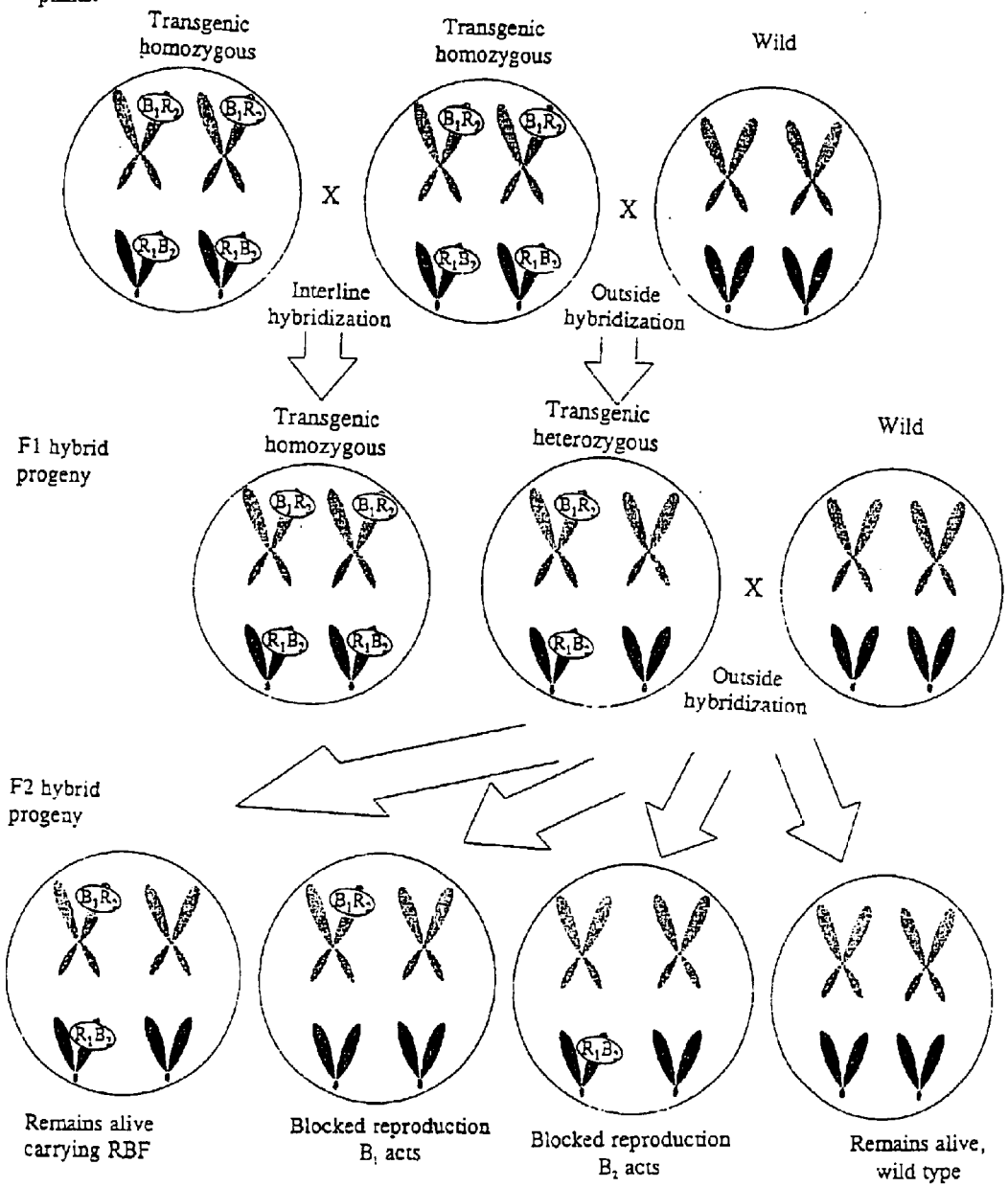
FIG. 7 depicts schematically hybridization of transgenic plants carrying a reversed delayed RBF (RD-RBF) construct FIGS. 8-I through 8-III depicts the three DNA constructs placed in three different chromosomes in triple RBF.

FIG. 7. Schematic hybridization of transgenic plants carrying reversed delayed RBF (RD-RBF) construct. The constructs of the first RBF is shown as B1 and R1 for blocking and recovering constructs respectively. B2 and R2 constructs belong to the second RBF. The blocking and recovering constructs are placed in different non-allelic chromosomes in opposite order. TGI is not shown in the figure. It can be linked either to the first (B1) or the second (B2) blocking construct. It is possible that two different TGIs are linked to the both blocking construct. As in the case of delayed RBF the intraline hybridization support homozygous genotype of the both RBF in progenies. F1 outside hybrid progeny carry heterozygous genotype for both RBF. The plants of the progeny are able to reproduction. Segregation of the constructs in F2 outside hybrid progeny is analogous to delayed RBF. No transgenic construct, however, can freely hybridize with wild relatives.

FIG. 8-I through 8-III. The molecular constructs described in the example No.7 is presented. The constructs are drawn to show the principle disposition of the genes. The abbreviations are p-promoter, 3' or polyA-3' end of the gene (polyadenylation site). Boxes of promoters show the direction of the gene sequences.

Figure 9:
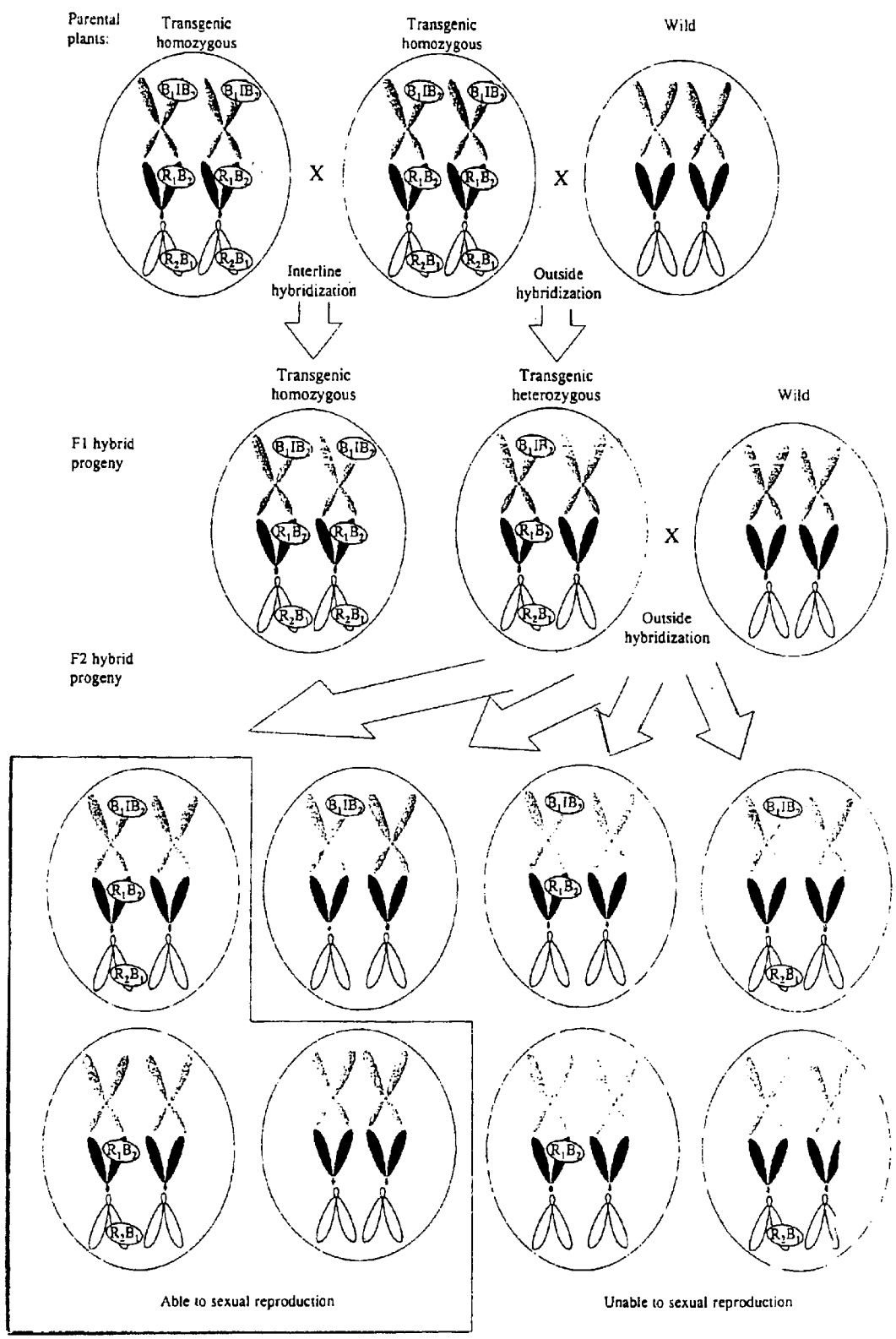
FIG. 9 depicts schematically the hybridization of transgenic plants carrying a triple RBF construct.

FIG. 9. Schematic hybridization of transgenic plants carrying triple RBF construct. The constructs of the first RBF are shown as B1 and R1 for blocking and recovering constructs respectively. B2 and R2 constructs belong to the second RBF. The blocking and recovering constructs are placed in different non-allelic chromosomes in opposite order and linked in pairs R1+B2 and R2+B1. Transgene of interest (I) is placed in the third non-allelic chromosome. It is situated between the first (B1) and the second (B2) blocking construct. The intraline hybridization support homozygous genotype of the both RBF in progenies. F1 outside hybrid progeny carry heterozygous genotype for all RBF constructs and the gene of interest. The plants of the progeny are able to reproduction. Segregation of the constructs in F2 outside hybrid progeny leads to a strong negative selection of the plants carrying the gene of interest. Only one from eight hybrid genotypes is able to sexual reproduction and carries the transgene of interest. No transgenic construct can freely hybridize with wild relatives.

Figure 10:
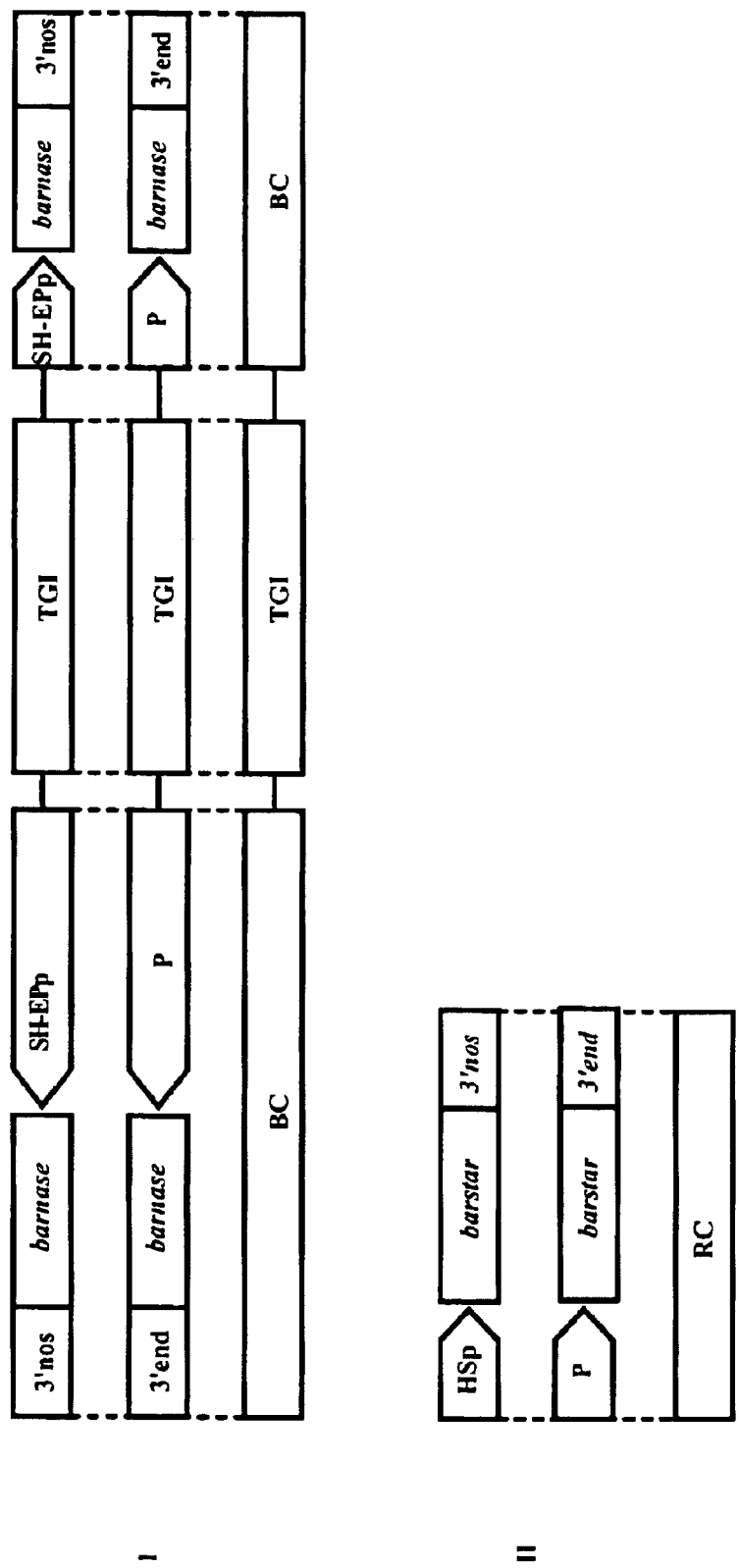
FIG. 10(A, B, C, D) depicts molecular constructs of double RBF.
Figure 10:
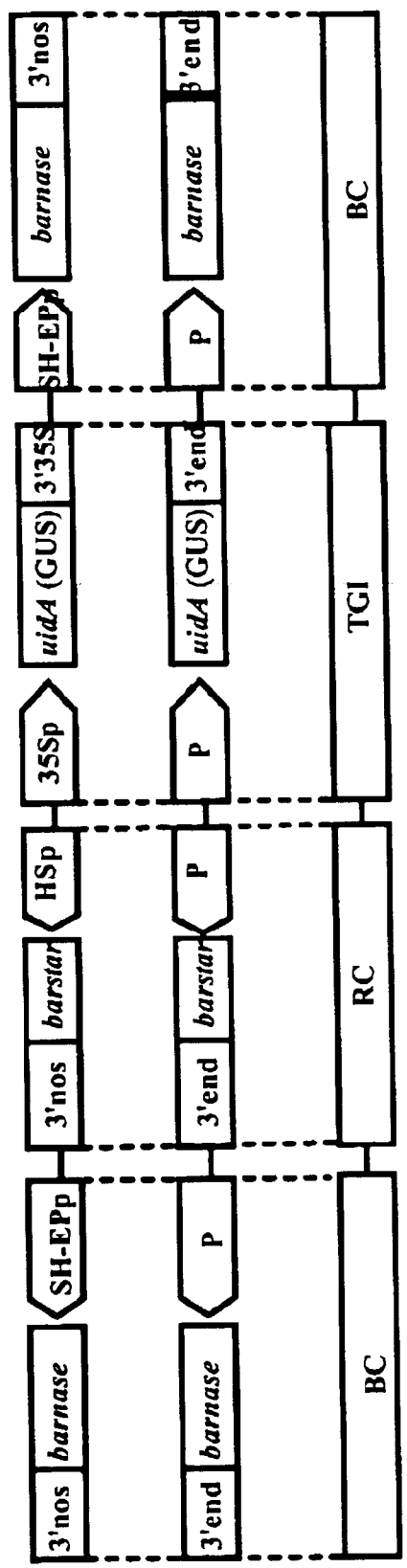
Figure 10:
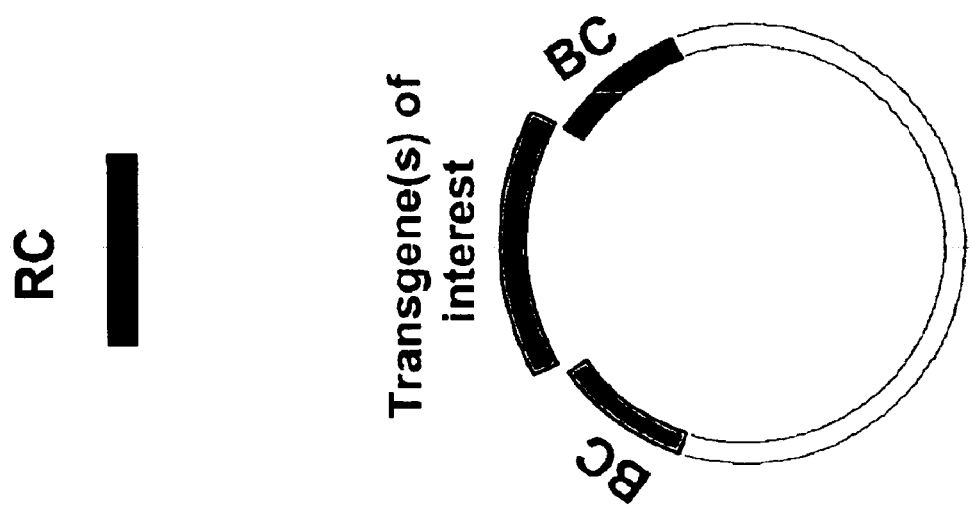
Figure 10:
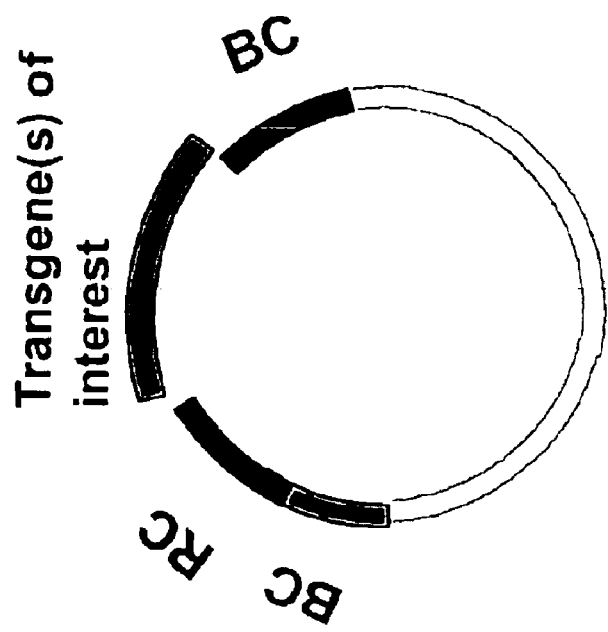

FIG. 10A shows two BCs flanking the TGI. Both the BCs have a nucleotide sequence encoding a barnase controlled by a SH-EPp promoter. The RC encodes for barstar and is controlled by a heat shock inducible promoter. The RC is located in a separate chromosome.

FIG. 10B shows two BCs flanking the TGI. Both the BCs have a nucleotide sequence encoding a barnase controlled by a SH-EPp promoter. The RC encodes barstar and it is controlled by a heat shock inducible promoter. The RC is located in the same transgenic insert as the BCs and the TGI.

FIG. 10C shows the BCs flanking the TGI. The TGI has been placed in a polycloning site of a vector. The BCs are placed into the vector first, thereafter the polycloning site and then the TGI is inserted. The RC is in a separate construct and is transformed separately from the BC-TGI-BC containing construct.

FIG. 10D shows the vector when the RC is in the same insert as the BCs. In this case the TGI is placed in the vector after the BC-R-BC construct and the Polycloning site.

References

U.S. Pat. No. 5,498,533 Poovaiah, et al. 1996, Control of growth and development of potato plants. Assignee Washington State University Research Foundation U.S. Pat. No. 5,723,765 Oliver et al. 1998, Control of plant gene expression. Assignee Delta and Pine Land Co.

U.S. Pat. No. 5,728,926 Fabijanski, et al. 1998, Antisense gene systems pollination control for hybrid seed production. Assignee Pioneer Hi-Bred International, Inc.

U.S. Pat. No. 5,750,867 Williams et al. 1998, Maintenance of male-sterile plants. Assignee Plant Genetic Systems, N.V.

U.S. Pat. No. 5,767,374 De Greef, et al. 1998, Plants with modified flowers seeds or embryos. Assignee Plant Genetic Systems, N. Y.

U.S. Pat. No. 5,880,333 Goff, et al. 1999, Control of the gene expression in plants by receptor-mediated transactivation in the presence of a chemical ligand. Assignee Novartis Finance Corporation (New York, N.Y.)

U.S. Pat. No. 6,005,167 Van Tunen, et al. 1999, Male-sterile plants, method for obtaining male-sterile plants and recombinant DNA for use therein. Assignee Mogen International N.V.

U.S. Pat. No. 6,013,859 Fabijanski, et al. 2000, Molecular methods of hybrid seed production Assignee Pioneer Hi-Bred International, Inc.

U.S. Pat. No. 6,022,720 Martinou, et al., 2000, Bax protein channel formation. Assignee Glaxo Wellcome Inc. Ainley and Key, 1990, Plant Mol. Biol. 14: 949–967

Akasofu et al., 1990, Nucl. Acid Res. 18: 1892

Barthelemy, et al., 1993, J. Biol. Chem. 268: 6546548

Beclin, et al., 1993, Transgenic Res. 2: 48–55

Cejudo et al., 1992, Plant Mol. Biol. 20: 849–856

Condit, et al., 1983, J. Mol. Appl. Gen. (USA), 2: 301–314

Czako and An, 1991, Plant Physiol. (Bethesda) 95:687–692

De Block and Debrouwer, (1993) Planta, 189: 218–225.

De Greve, et al., 1985 J. Mol. Appl. Gen. (USA), 1: 499–511

Depicker, et al., 1982, J. Mol. Appl. Gen. (USA), 1: 561–573

Devic, et al., 1996, Plant 9: 205–2015

Filpula, et al., 1988, Nucl. Acid Res. 16: 10385

Galau, et al., 1992, Plant Physiol. 99: 783–788

Gatz and Quail, 1988, Proc. Natl. Acad. Sci. USA, 85: 1394–1397
Gatz, et al., 1991, Mol. Gen. Genet. 227: 229–237
Graham et al., 1992, Plant Cell 4: 349–357
Graham et al., 1994, Plant Cell 6: 761–772
Hamza, et al. 1993, Theor. App:. Gen. 86: 657–664
Hartley, 1989, Trends Biochem. Sci. 14: 450–454
Hudspeth, et al., 1996, Plant Mol. Biol. 31: 701–705
Hughes and Galau, 1989, (Lea promoter): Genes and Development 3: 358–369
Ito, et al. 1994, Mol. Gen. Genet. 245:1–10
Janssen, 1995, Plant Physiol. 108: 1339
Koning et al. 1992, Plant mol. Biol. 18: 247–258
Lanzer, et al., 1988, Proc. Natl. Acad. Sci. USA, 85: 8973–8977
Madhusoodana, et al., 1998, J. Cell. Physiol. 176: 40–49
Mariani, et al., 1990, Nature 347: 737–741
Mariani, et al., 1992, Nature, 357: 384–387
McAlister, et al., 1998, Australian J. Plant Physiol. 25: 225–235
Minamikava et al., 1992, Plant Cell Physiol. 33: 253–258
Nillson, et al., 1998, Plant J. 15: 799–804
Ogushi et al., 1992, Plant Mol. Biol. 19: 705–706
Ohshima, et al., 1990, Plant Cell 2: 95–106
Payne, et al., 1988, Plant Mol. Biol. 11: 89–94
Pfitzner, et al., 1988, Mol. Gen. Genet. 211: 290–295
Popham, et al. 1995, Physiol. Mol. Plant Pathology, 47:39–50
Rahmatullah et al., 1989, Plant mol. Biol. 12: 119–121
Ramakrishnan and Joseph, 1996. Canadian J. Microbiol. 42: 316–325
Reynolds and Smith, 1995, Plant Mol. Biol. 27: 487497
Sarah et al., 1996, Mol. Gen. Genet. 250: 153–161
Sun and Kamiya, 1994, Plant Cell, 6: 1509–1518
Temple, et al., 1993, Mol. Gen. Genet. 236: 315–325
Turley and Trelease, 1990, Plant Mol. Biol. 14: 137–146
Twell, 1995, Protoplasma, 187: 144–154
Van de Rhee, et al., 1990, Plan Mol. Biol. 21:451–461
Van Der Geest, et al., 1996, Plant Physiol. (Rockville) 109: 1151–1158
Vogeli-Lange et al., 1994, Plant J. 5: 273–27
Williamson, et al., 1989, Plant Physiol., 90: 1570–1576
Yamauchi et al., 1996, Plant Mol. Biol. 30: 321–329
Zaitlin, et al., 1985, Biotechnology in plant science: relevance to agriculture in the eighties.
Orlando, Fla. (USA). Academic press, 227–235
Zhang et al., 1994, Plant Physiol. 104: 875–864.

SEQUENCE LISTING

```
<160> NUMBER OF SEQ ID NOS: 15

<210> SEQ ID NO 1
<211> LENGTH: 357
<212> TYPE: DNA
<213> ORGANISM: Artificial Sequence
<220> FEATURE:
<223> OTHER INFORMATION: Description of Artificial Sequence: Bacillus
      amyloliquefaciens
<223> OTHER INFORMATION: Description: Plant adapted synthetic coding
      sequence of barnase gene.
<223> OTHER INFORMATION: Fragment type: Full coding sequence.

<400> SEQUENCE: 1
cgcggatcca tggcacaagt tatcaacacc tttgatggag ttgctgacta ccttcagacc      60
taccataagc ttccagataa ctacatcacc aagtctgagg ctcaggctct tggatgggtt    120
gcttctaagg gaaaccttgc tgatgtcgct ccaggaaagt ctatcggagg tgatatcttc    180
tctaacaggg agggaaagct tccaggaaag tctgaaggga cctggaggga ggctgatatc    240
aactacacct ctggattcag gaactctgat aggatccttt actcttccga ctggcttatc    300
tacaagacca ctgaccacta ccagaccttc accaagatcc ggtgagagct cgagcgc      357

<210> SEQ ID NO 2
<211> LENGTH: 299
<212> TYPE: DNA
<213> ORGANISM: Artificial Sequence
<220> FEATURE:
<223> OTHER INFORMATION: Description of Artificial Sequence: Bacillus
      amyloliquefaciens
<223> OTHER INFORMATION: Description: Plant adapted synthetic coding
      sequence of barstar gene.
<223> OTHER INFORMATION: Fragment type: Full coding sequence.

<400> SEQUENCE: 2
cgcggatcct gatcatgaag aaggctgtta tcaacggtga gcaaattagg tctatctctg      60
atcttcacca gacccttaag aaggagcttg ctcttccaga gtactacgga gagaaccttg    120
```

-continued

```
atgctctatg ggattgcctt accggatggg tggagtaccc acttgttttg gagtggaggc      180
agtttgagca gtctaagcag cttactgaga atggagctga gagtgttctt caggttttcc      240
gggaggctaa ggctgaggga tgcgatatca ccatcattct ttcttgagag ctcgagcgc       299
```

<210> SEQ ID NO 3
<211> LENGTH: 856
<212> TYPE: DNA
<213> ORGANISM: Artificial Sequence
<220> FEATURE:
<223> OTHER INFORMATION: Description of Artificial Sequence: Vigna mungo
      (SH-EP promoter), Bacillus amyloliquefaciens (barnase gene),
      Escherichia coli (uidA gene)
<221> NAME/KEY: promoter
<222> LOCATION: (1)..(352)
<223> OTHER INFORMATION: Modified SH-EP promoter.
<221> NAME/KEY: misc_feature
<222> LOCATION: (353)..(404)
<223> OTHER INFORMATION: 5' end exon of modified uidA gene.
<221> NAME/KEY: misc_feature
<222> LOCATION: (443)..(778)
<223> OTHER INFORMATION: Synthetic coding sequence of barnase gene.
<221> NAME/KEY: intron
<222> LOCATION: (405)..(830)
<223> OTHER INFORMATION: Intron of uidA gene.
<221> NAME/KEY: misc_feature
<222> LOCATION: (831)..(856)
<223> OTHER INFORMATION: Exon of modified uidA gene.

<400> SEQUENCE: 3

```
cagcatgcaa gagaaagatg attcttgaag catacgataa cagattgaat gtgacaaaaa      60
gtttgtgtct cagcttcagg gtcggcacct aatacaaaag gaaaatttgt caggttttcct    120 tccgtagttt cattcactat tattgaatcc tttggctacc attcttgaga aacacaaaca     180
cttcttatat ctgttctaca caattctctg agtgcgtgcc acagtttggt atcttcatga     240
ttgctcattg ttcatgccca taaggaacat gtaacttcct catttattta ttattgcttt     300
tgttttcttc tcactagttt acaaacgttt ccctatataa accctccttt gttcactgct     360
ttcctccctg ttgtggcttc tctccgaagt tcatcccggt ccacctgcaa aataagtaat     420
aagataaagt aaaaaagtta gtatggctca agttattaat acttttgatg gagttgctga     480
ttatcttcaa acttatcata aacttccaga taattatatt actaaatctg aagctcaagc     540
tcttggatgg gttgcttcta aaggaaatct tgctgatgtt gctccaggaa aatctattgg     600
aggagatatt ttttcaaata gagaaggaaa acttccagga aaatctggaa gaacatggag     660
agaagctgat attaattata cttctggatt tagaaattca gatagaatcc tttattcatc     720
tgattggctt atttataaaa ctacagatca ttatcaaact tttacaaaaa ttagataaat     780
atttgtgttt tttgtatgtt gtgatcatta ataaataaat aaatacatac ctcttctgca     840
gcaggaaggc agccga                                                     856
```

<210> SEQ ID NO 4
<211> LENGTH: 249
<212> TYPE: DNA
<213> ORGANISM: Artificial Sequence
<220> FEATURE:
<223> OTHER INFORMATION: Description of Combined DNA/RNA Molecule: -
<223> OTHER INFORMATION: Description of Artificial Sequence: -
<223> OTHER INFORMATION: Description: Synthetic polycloning site for
      plasmid DNA.

<400> SEQUENCE: 4

```
aagcttacta gtggtaccac cggtacgcgt gggcccgcat gctgatcaat gcatgtcgac      60
catatggccg gcgctagcca attggacgtc cttaagatcg atccgcggct gcaggcgcgc     120
```

-continued

```
ggatcccgta cgccatggcg gccgggcgcc gagctcgtgc actctagacc cgggggcgcg      180
ccctcgagtg tacatcatga gcggccgcag atctggccgg cctttaatta atccggacct      240
agggaattc                                                              249
```

<210> SEQ ID NO 5
<211> LENGTH: 8
<212> TYPE: DNA
<213> ORGANISM: Artificial Sequence
<220> FEATURE:
<223> OTHER INFORMATION: Description of Combined DNA/RNA Molecule: -
<223> OTHER INFORMATION: Description of Artificial Sequence: -
<223> OTHER INFORMATION: 5' exon/intron boundary site.

<400> SEQUENCE: 5

```
agguaugu                                                                8
```

<210> SEQ ID NO 6
<211> LENGTH: 7
<212> TYPE: DNA
<213> ORGANISM: Artificial Sequence
<220> FEATURE:
<223> OTHER INFORMATION: Description of Combined DNA/RNA Molecule: -
<223> OTHER INFORMATION: Description of Artificial Sequence: -
<223> OTHER INFORMATION: Branchpoint sequence, located 20-50 nt upstream
      from boundary site.

<400> SEQUENCE: 6

```
uacuaac                                                                 7
```

<210> SEQ ID NO 7
<211> LENGTH: 5
<212> TYPE: DNA
<213> ORGANISM: Artificial Sequence
<220> FEATURE:
<223> OTHER INFORMATION: Description of Combined DNA/RNA Molecule: -
<223> OTHER INFORMATION: Description of Artificial Sequence: -
<223> OTHER INFORMATION: 3' intron/exon boundary site.

<400> SEQUENCE: 7

```
gcagg                                                                   5
```

<210> SEQ ID NO 8
<211> LENGTH: 6
<212> TYPE: DNA
<213> ORGANISM: Artificial Sequence
<220> FEATURE:
<223> OTHER INFORMATION: Description of Combined DNA/RNA Molecule: -
<223> OTHER INFORMATION: Description of Artificial Sequence: -
<223> OTHER INFORMATION: Polyadenylation signal in transcription unit
      near the upstream element (NUE).

<400> SEQUENCE: 8

```
aauaaa                                                                  6
```

<210> SEQ ID NO 9
<211> LENGTH: 6
<212> TYPE: DNA
<213> ORGANISM: Artificial Sequence
<220> FEATURE:
<223> OTHER INFORMATION: Description of Combined DNA/RNA Molecule: -
<223> OTHER INFORMATION: Description of Artificial Sequence: -
<223> OTHER INFORMATION: Upstream FUE element.

<400> SEQUENCE: 9

```
uuugua                                                                  6
```

```
<210> SEQ ID NO 10
<211> LENGTH: 10
<212> TYPE: DNA
<213> ORGANISM: Artificial Sequence
<220> FEATURE:
<223> OTHER INFORMATION: Description of Combined DNA/RNA Molecule: -
<223> OTHER INFORMATION: Description of Artificial Sequence: -
<223> OTHER INFORMATION: Upstream FUE element.

<400> SEQUENCE: 10
uguguuuuuu                                                              10

<210> SEQ ID NO 11
<211> LENGTH: 7
<212> TYPE: DNA
<213> ORGANISM: Artificial Sequence
<220> FEATURE:
<223> OTHER INFORMATION: Description of Combined DNA/RNA Molecule: -
<223> OTHER INFORMATION: Description of Artificial Sequence: -
<223> OTHER INFORMATION: Upstream FUE element.

<400> SEQUENCE: 11 uguugug                                                                  7

<210> SEQ ID NO 12
<211> LENGTH: 13
<212> TYPE: DNA
<213> ORGANISM: Artificial Sequence
<220> FEATURE:
<223> OTHER INFORMATION: Description of Combined DNA/RNA Molecule: -
<223> OTHER INFORMATION: Description of Artificial Sequence: -
<221> NAME/KEY: promoter
<222> LOCATION: ()
<223> OTHER INFORMATION: Promoter region located 15-60 nucleotides from
      the start of the transcription with TATA in consensus sequence.

<400> SEQUENCE: 12
tcactatata tag                                                          13

<210> SEQ ID NO 13
<211> LENGTH: 4
<212> TYPE: DNA
<213> ORGANISM: Artificial Sequence
<220> FEATURE:
<223> OTHER INFORMATION: Description of Combined DNA/RNA Molecule: -
<223> OTHER INFORMATION: Description of Artificial Sequence: -
<223> OTHER INFORMATION: Box located 30-100 nucleotides upstream the
      TATA box.

<400> SEQUENCE: 13 caat                                                                     4

<210> SEQ ID NO 14
<211> LENGTH: 4
<212> TYPE: DNA
<213> ORGANISM: Artificial Sequence
<220> FEATURE:
<223> OTHER INFORMATION: Description of Combined DNA/RNA Molecule: -
<223> OTHER INFORMATION: Description of Artificial Sequence: -
<223> OTHER INFORMATION: Box located 30-100 nucleotides upstream the
      TATA box.

<400> SEQUENCE: 14 agga                                                                     4

<210> SEQ ID NO 15
<211> LENGTH: 10
<212> TYPE: DNA
```

```
<213> ORGANISM: Artificial Sequence
<220> FEATURE:
<223> OTHER INFORMATION: Description of Artificial Sequence: -
<223> OTHER INFORMATION: Sequence 40-80 nt downstream from the AUG codon
      starting.

<400> SEQUENCE: 15
aacaatggct                                                              10
```

What is claimed is:

1. A method for controlling transgene segregation in a sexually reproducing transgenic plant and for preventing transgene escape by providing a plant with a recoverable block of function (RBF) system, said system comprising:

two functionally similar blocking constructs (BCs) under control of germination/embryo development specific promoters, each of said BCs comprising a nucleotide sequence encoding an entire barnase protein and having a capacity to block at least one molecular or physiological function essential for the development and/or reproductive cycle of the transgenic plant, thereby leading to death or incapacity of sexual reproduction;

a transgene of interest (TGI) being inserted between the two BCs; and a user-controlled means for recovering functions blocked by the BCs, said means for recovering comprising an externally applicable and controllable manipulation, treatment or intervention step and a recovering construct (RC) being under control of a heat shock inducible promoter, said RC further comprising a nucleotide sequence encoding an entire barstar protein.

2. The method according to claim 1, wherein the BCs are placed in same chromosome as the RC.

3. The method according to claim 1, wherein the nucleotide sequence encoding barnase is synthetic.

4. The method according to claim 3, wherein the synthetic nucleotide sequence comprises SEQ ID NO:1.

5. The method according to claim 1, wherein the RC is placed in a non-allelic chromosome apart from the BCs and the TGI.

6. A DNA construct for controlling transgene segregation and/or for preventing the escape of a transgene into the environment, said DNA construct comprising:

two functionally similar blocking constructs (BCs) driven by germination/embryo development specific promoters, said BCs being recoverable by an external, artificial, controllable means for recovering, both of said BCs further containing a nucleotide sequence capable of blocking a certain molecular or physiological function of a transgenic plant, thereby leading to death or incapacity of sexual reproduction, said nucleotide sequence further encoding an entire barnase protein;

a transgene of interest (TGI) encoding a desired gene product, said TGI being inserted between the two BCs and;

one or more recovering constructs (RCs), said RCs comprising a nucleotide sequence encoding an entire barstar protein and being under control of a heat shock inducible promoter and thereby being capable of external regulation.

7. The DNA construct according to claim 6, wherein the BCs comprise a synthetic nucleotide sequence, said synthetic nucleotide sequence being adapted to plant preference.

8. The DNA construct according to claim 6 comprising two BCs in a cloning vector and a polycloning site for inserting the TGI between said two BCs.

9. The DNA construct according to claim 8, wherein the polycloning site is synthetic.

10. The DNA construct according to claim 8, wherein the polycloning site is SEQ ID NO:4.

11. A cloning vector comprising one or more DNA constructs of claim 6 further comprising a polycloning site for inserting the TGI between the two BCs.

12. A transgenic plant cell comprising one or more of the DNA constructs according to claim 6.

13. A cell-line comprising a plant cell having one or more of the DNA construct according to claim 6.

14. A transgenic plant transformed with one or more of the DNA construct according to claim 6.

15. A method for controlling transgene segregation in a sexually reproducing transgenic plant and for preventing transgene escape by providing a plant with a recoverable block of function (RBF) system comprising:

a blocking construct (BC), said BC comprising a synthetic barnase coding sequence, said synthetic barnase coding sequence flanking a transgene of interest (TGI), said BC further being driven by a germination/embryo development specific promoter and;

a recovering construct (RC), said RC comprising a synthetic barstar coding sequence and being driven by a heat shock inducible promoters.

16. The method according to claim 15, wherein the synthetic barnase coding sequence comprises the sequence according to SEQ ID NO:1.

17. The method according to claim 15, wherein the synthetic barstar coding sequence comprises the sequence according to SEQ ID NO:2.

18. The method according to claim 15, wherein the germination specific promoter is a cysteine endopeptidase promoter.

19. A DNA construct for controlling transgene segregation and/or for preventing the escape of a transgene into the environment, said DNA construct comprising:

a blocking construct (BC), said BC being recoverable by an external, artificial, controllable means for recovering, said BC further containing a nucleotide sequence encoding barnase and being capable of blocking a certain molecular or physiological function of a transgenic plant, thereby leading to death or incapacity of sexual reproduction, said nucleotide sequence being closely linked to a transgene of interest (TGI) encoding a desired gene product and;

a recovering construct (RC) capable of being externally regulated and comprising a nucleotide sequence encoding barstar, said RC being under control of a heat shock inducible promoter.

20. The DNA construct according to claim 19, wherein the BC comprises a synthetic barnase coding sequence.

21. The DNA construct according to claim 20, wherein the synthetic barnase coding sequence is SEQ ID NO:1.

22. The DNA construct according to claim 19, wherein the barstar coding sequence is SEQ ID NO:2.

23. A transgenic plant cell comprising one or more of the DNA constructs according to claim 19.

24. A cell-line comprising a plant cell having one or more of the DNA construct according to clam 19.

25. A transgenic plant transformed with one or more of the DNA construct according to claim 19.

* * * * *